US012741090B2

(12) United States Patent
Lee et al.

(10) Patent No.: US 12,741,090 B2
(45) Date of Patent: Sep. 22, 2026

(54) AUTOMATIC DRUG DELIVERY SYSTEM HAVING MULTIPLE COMMUNICATION OPTIONS

(71) Applicant: INSULET CORPORATION, Acton, MA (US)

(72) Inventors: Joon Bok Lee, Acton, MA (US); Yibin Zheng, Hartland, WI (US); Jason O'Connor, Acton, MA (US); Ashutosh Zade, San Diego, CA (US); James Causey, Simi Valley, CA (US)

(73) Assignee: INSULET CORPORATION, Acton, MA (US)

( * ) Notice: Subject to any disclaimer, the term of this patent is extended or adjusted under 35 U.S.C. 154(b) by 616 days.

(21) Appl. No.: 18/192,380

(22) Filed: Mar. 29, 2023

(65) Prior Publication Data

US 2023/0310741 A1 Oct. 5, 2023

Related U.S. Application Data

(60) Provisional application No. 63/325,867, filed on Mar. 31, 2022.

(51) Int. Cl.
*A61M 5/172* (2006.01)

(52) U.S. Cl.
CPC ......... *A61M 5/172* (2013.01); *A61M 2205/50* (2013.01)

(58) Field of Classification Search
CPC .... A61M 5/172; A61M 2205/50; H04W 4/80; G16H 20/13; G16H 20/17; G16H 40/60; G16H 20/10
See application file for complete search history.

(56) References Cited

U.S. PATENT DOCUMENTS

| | | | |
|---|---|---|---|
| 303,013 | A | 8/1884 | Horton |
| 441,663 | A | 12/1890 | Hofbauer |
| 955,911 | A | 4/1910 | Saegmuller |
| 1,441,508 | A | 1/1923 | Marius |
| 2,797,149 | A | 6/1957 | Skeggs |
| 2,987,214 | A | 6/1961 | Radack |
| 3,579,805 | A | 5/1971 | Kast |
| 3,631,847 | A | 1/1972 | Hobbs |
| 3,634,039 | A | 1/1972 | Brondy |
| 3,812,843 | A | 5/1974 | Wootten et al. |
| 3,841,328 | A | 10/1974 | Jensen |

(Continued)

FOREIGN PATENT DOCUMENTS

| | | | |
|---|---|---|---|
| AU | 2015200834 | A1 | 3/2015 |
| AU | 2015301146 | A1 | 3/2017 |

(Continued)

OTHER PUBLICATIONS

US 5,954,699 A, 09/1999, Jost et al. (withdrawn)

(Continued)

*Primary Examiner* — Sharad Rampuria
(74) *Attorney, Agent, or Firm* — Goodwin Procter LLP

(57) ABSTRACT

Disclosed herein is a drug delivery system wherein wearable components of the system are provided with Wi-Fi and/or cellular capabilities such as to allow different modalities for inter-component communications and, further, to allow access to a plethora of cloud-based services to enhance the functionality of the system.

11 Claims, 5 Drawing Sheets

(56) References Cited

U.S. PATENT DOCUMENTS 3,963,380 A 6/1976 Thomas, Jr. et al.
4,055,175 A 10/1977 Clemens et al.
4,146,029 A 3/1979 Ellinwood, Jr.
4,151,845 A 5/1979 Clemens
4,206,401 A 6/1980 Meyer
4,245,634 A 1/1981 Albisser et al.
4,277,226 A 7/1981 Archibald
4,307,713 A 12/1981 Galkin et al.
4,368,980 A 1/1983 Aldred et al.
4,373,527 A 2/1983 Fischell
4,398,542 A 8/1983 Cunningham et al.
4,403,984 A 9/1983 Ash et al.
4,464,170 A 8/1984 Clemens et al.
4,469,481 A 9/1984 Kobayashi
4,475,901 A 10/1984 Kraegen et al.
4,526,568 A 7/1985 Clemens et al.
4,526,569 A 7/1985 Bernardi
4,529,401 A 7/1985 Leslie et al.
4,559,033 A 12/1985 Stephen et al.
4,559,037 A 12/1985 Franetzki et al.
4,560,979 A 12/1985 Rosskopf
4,573,968 A 3/1986 Parker
4,587,850 A 5/1986 Moser
4,624,661 A 11/1986 Arimond
4,633,878 A 1/1987 Bombardieri
4,657,529 A 4/1987 Prince et al.
4,685,903 A 8/1987 Cable et al.
4,731,726 A 3/1988 Allen, III
4,743,243 A 5/1988 Vaillancourt
4,755,173 A 7/1988 Konopka et al.
4,781,688 A 11/1988 Thoma et al.
4,781,693 A 11/1988 Martinez et al.
4,801,957 A 1/1989 Vandemoere
4,808,161 A 2/1989 Kamen
4,833,088 A 5/1989 Desimone et al.
4,836,752 A 6/1989 Burkett
4,850,954 A 7/1989 Charvin
4,854,170 A 8/1989 Brimhall et al.
4,882,600 A 11/1989 Van de Moere
4,886,499 A 12/1989 Cirelli et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,961,055 A 10/1990 Habib et al.
4,973,998 A 11/1990 Gates
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,045,871 A 9/1991 Reinholdson
5,097,834 A 3/1992 Skrabal
5,102,406 A 4/1992 Arnold
5,109,850 A 5/1992 Blanco et al.
5,125,415 A 6/1992 Bell
5,134,079 A 7/1992 Cusack et al.
5,153,827 A 10/1992 Coutre et al.
5,165,406 A 11/1992 Wong
5,176,662 A 1/1993 Bartholomew et al.
5,178,609 A 1/1993 Ishikawa
5,207,642 A 5/1993 Orkin et al.
5,232,439 A 8/1993 Campbell et al.
5,232,668 A 8/1993 Grant et al.
5,237,993 A 8/1993 Skrabal
5,239,326 A 8/1993 Takai
5,244,459 A 9/1993 Hill
5,244,463 A 9/1993 Cordner, Jr. et al.
5,257,980 A 11/1993 Van Antwerp et al.
5,273,517 A 12/1993 Barone et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,377,674 A 1/1995 Kuestner
5,380,665 A 1/1995 Cusack et al.
5,385,539 A 1/1995 Maynard
5,389,078 A 2/1995 Zalesky
5,411,889 A 5/1995 Hoots et al.
5,421,812 A 6/1995 Langley et al.
5,452,033 A 9/1995 Balling et al.
5,468,727 A 11/1995 Phillips et al.
5,505,709 A 4/1996 Funderburk et al.
5,505,828 A 4/1996 Wong et al.
5,507,288 A 4/1996 Bocker et al.
5,533,389 A 7/1996 Kamen et al.
5,558,640 A 9/1996 Pfeiler et al.
5,563,584 A 10/1996 Rader et al.
5,569,186 A 10/1996 Lord et al.
5,576,781 A 11/1996 Deleeuw
5,584,813 A 12/1996 Livingston et al.
5,585,733 A 12/1996 Paglione
5,586,553 A 12/1996 Halili et al.
5,609,572 A 3/1997 Lang
5,647,853 A 7/1997 Feldmann et al.
5,660,163 A 8/1997 Schulman et al.
5,665,065 A 9/1997 Colman et al.
5,678,539 A 10/1997 Schubert et al.
5,685,844 A 11/1997 Marttila
5,685,859 A 11/1997 Kornerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,714,123 A 2/1998 Sohrab
5,716,343 A 2/1998 Kriesel et al.
5,722,397 A 3/1998 Eppstein
5,726,404 A 3/1998 Brody
5,726,751 A 3/1998 Altendorf et al.
5,741,228 A 4/1998 Lambrecht et al.
5,746,217 A 5/1998 Erickson et al.
5,755,682 A 5/1998 Knudson et al.
5,758,643 A 6/1998 Wong et al.
5,785,681 A 7/1998 Indravudh et al.
5,800,405 A 9/1998 McPhee
5,800,420 A 9/1998 Gross et al.
5,801,057 A 9/1998 Smart et al.
5,804,048 A 9/1998 Wong et al.
5,817,007 A 10/1998 Fodgaard et al.
5,820,622 A 10/1998 Gross et al.
5,823,951 A 10/1998 Messerschmidt
5,830,999 A 11/1998 Dunn
5,840,020 A 11/1998 Heinonen et al.
5,848,991 A 12/1998 Gross et al.
5,851,197 A 12/1998 Marano et al.
5,858,005 A 1/1999 Kriesel
5,865,806 A 2/1999 Howell
5,867,688 A 2/1999 Simmon et al.
5,871,470 A 2/1999 McWha
5,879,310 A 3/1999 Sopp et al.
5,899,882 A 5/1999 Waksman et al.
5,902,253 A 5/1999 Pfeiffer et al.
5,931,814 A 8/1999 Alex et al.
5,932,175 A 8/1999 Knute et al.
5,935,099 A 8/1999 Peterson et al.
5,947,911 A 9/1999 Wong et al.
5,971,941 A 10/1999 Simons et al.
5,993,423 A 11/1999 Choi
5,995,236 A 11/1999 Roth et al.
5,997,501 A 12/1999 Gross et al.
6,017,318 A 1/2000 Gauthier et al.
6,024,539 A 2/2000 Blomquist
6,032,059 A 2/2000 Henning et al.
6,036,924 A 3/2000 Simons et al.
6,040,578 A 3/2000 Malin et al.
6,049,727 A 4/2000 Crothall
6,050,978 A 4/2000 Orr et al.
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.

(56) References Cited

U.S. PATENT DOCUMENTS 6,102,872 A 8/2000 Doneen et al.
6,115,673 A 9/2000 Malin et al.
6,123,827 A 9/2000 Wong et al.
6,124,134 A 9/2000 Stark
6,126,637 A 10/2000 Kriesel et al.
6,128,519 A 10/2000 Say
6,142,181 A 11/2000 Schumacher
6,142,939 A 11/2000 Eppstein et al.
6,143,164 A 11/2000 Heller et al.
6,157,041 A 12/2000 Thomas et al.
6,161,028 A 12/2000 Braig et al.
6,162,639 A 12/2000 Douglas
6,171,264 B1 1/2001 Bader
6,196,046 B1 3/2001 Braig et al.
6,200,287 B1 3/2001 Keller et al.
6,200,293 B1 3/2001 Kriesel et al.
6,200,338 B1 3/2001 Solomon et al.
6,214,629 B1 4/2001 Freitag et al.
6,226,082 B1 5/2001 Roe
6,244,776 B1 6/2001 Wiley
6,261,065 B1 7/2001 Nayak et al.
6,262,798 B1 7/2001 Shepherd et al.
6,270,455 B1 8/2001 Brown
6,271,045 B1 8/2001 Douglas et al.
6,280,381 B1 8/2001 Malin et al.
6,285,448 B1 9/2001 Kuenstner
6,309,370 B1 10/2001 Haim et al.
6,312,888 B1 11/2001 Wong et al.
6,334,851 B1 1/2002 Hayes et al.
6,375,627 B1 4/2002 Mauze et al.
6,379,301 B1 4/2002 Worthington et al.
6,381,029 B1 4/2002 Tipirneni
6,402,689 B1 6/2002 Scarantino et al.
6,418,332 B1 7/2002 Mastrototaro et al.
6,470,279 B1 10/2002 Samsoondar
6,475,196 B1 11/2002 Vachon
6,477,901 B1 11/2002 Tadigadapa et al.
6,484,044 B1 11/2002 Lilienfeld-Toal
6,491,656 B1 12/2002 Morris
6,512,937 B2 1/2003 Blank et al.
6,514,460 B1 2/2003 Fendrock
6,525,509 B1 2/2003 Petersson et al.
6,528,809 B1 3/2003 Thomas et al.
6,540,672 B1 4/2003 Simonsen et al.
6,544,212 B2 4/2003 Galley et al.
6,546,268 B1 4/2003 Ishikawa et al.
6,546,269 B1 4/2003 Kurnik
6,553,841 B1 4/2003 Blouch
6,554,798 B1 4/2003 Mann et al.
6,556,850 B1 4/2003 Braig et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,618,603 B2 9/2003 Varalli et al.
6,633,772 B2 10/2003 Ford et al.
6,645,142 B2 11/2003 Braig et al.
6,653,091 B1 11/2003 Dunn et al.
6,662,030 B2 12/2003 Khalil et al.
6,669,663 B1 12/2003 Thompson
6,678,542 B2 1/2004 Braig et al.
6,685,452 B2 2/2004 Christiansen et al.
6,699,221 B2 3/2004 Vaillancourt
6,718,189 B2 4/2004 Rohrscheib et al.
6,721,582 B2 4/2004 Trepagnier et al.
6,728,560 B2 4/2004 Kollias et al.
6,740,059 B2 5/2004 Flaherty
6,740,072 B2 5/2004 Starkweather et al.
6,751,490 B2 6/2004 Esenaliev et al.
6,758,835 B2 7/2004 Close et al.
6,768,319 B2 7/2004 Wang
6,768,425 B2 7/2004 Flaherty et al.
6,780,156 B2 8/2004 Haueter et al.
6,810,290 B2 10/2004 Lebel et al.
6,830,558 B2 12/2004 Flaherty et al.
6,837,858 B2 1/2005 Cunningham et al.
6,837,988 B2 1/2005 Leong et al.
6,846,288 B2 1/2005 Nagar et al.
6,862,534 B2 3/2005 Sterling et al.
6,865,408 B1 3/2005 Abbink et al.
6,890,291 B2 5/2005 Robinson et al.
6,936,029 B2 8/2005 Mann et al.
6,949,081 B1 9/2005 Chance
6,958,809 B2 10/2005 Sterling et al.
6,989,891 B2 1/2006 Braig et al.
6,990,366 B2 1/2006 Say et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,060,059 B2 6/2006 Keith et al.
7,061,593 B2 6/2006 Braig et al.
7,096,124 B2 8/2006 Sterling et al.
7,115,205 B2 10/2006 Robinson et al.
7,128,727 B2 10/2006 Flaherty et al.
7,137,964 B2 11/2006 Flaherty
7,139,593 B2 11/2006 Kavak et al.
7,139,598 B2 11/2006 Hull et al.
7,144,384 B2 12/2006 Gorman et al.
7,171,252 B1 1/2007 Scarantino et al.
7,182,726 B2 2/2007 Williams et al.
7,190,988 B2 3/2007 Say et al.
7,204,823 B2 4/2007 Estes et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,303,073 B2 12/2007 Raynal-Olive et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,547,281 B2 6/2009 Hayes et al.
7,569,030 B2 8/2009 Ebel et al.
7,608,042 B2 10/2009 Goldberger et al.
7,651,845 B2 1/2010 Doyle, III et al.
7,680,529 B2 3/2010 Kroll
7,731,900 B2 6/2010 Haar et al.
7,734,323 B2 6/2010 Blomquist et al.
7,766,829 B2 8/2010 Sloan et al.
7,785,258 B2 8/2010 Braig et al.
7,806,854 B2 10/2010 Damiano et al.
7,806,886 B2 10/2010 Kanderian, Jr. et al.
7,842,241 B2 11/2010 Arbogast et al.
7,846,385 B2 12/2010 Arbogast et al.
7,846,386 B2 12/2010 Arbogast et al.
7,846,387 B2 12/2010 Arbogast et al.
7,846,388 B2 12/2010 Arbogast et al.
7,867,446 B2 1/2011 Arbogast et al.
7,897,107 B2 3/2011 Arbogast et al.
7,914,742 B2 3/2011 Arbogast et al.
7,918,825 B2 4/2011 OConnor et al.

(56) References Cited

U.S. PATENT DOCUMENTS 7,946,985 B2 5/2011 Mastrototaro et al.
7,972,296 B2 7/2011 Braig et al.
8,003,052 B2 8/2011 Sacherer
8,056,719 B2 11/2011 Porret et al.
8,080,205 B2 12/2011 Arbogast et al.
8,105,282 B2 1/2012 Susi et al.
8,221,345 B2 7/2012 Blomquist
8,251,907 B2 8/2012 Sterling et al.
8,285,487 B2 10/2012 Bergstrom et al.
8,431,408 B2 4/2013 Lewis et al.
8,449,524 B2 5/2013 Braig et al.
8,452,359 B2 5/2013 Rebec et al.
8,454,557 B1 6/2013 Qi et al.
8,454,576 B2 6/2013 Mastrototaro et al.
8,461,561 B2 6/2013 Freeman et al.
8,465,977 B2 6/2013 Joseph et al.
8,467,980 B2 6/2013 Campbell et al.
8,478,557 B2 7/2013 Hayter et al.
8,547,239 B2 10/2013 Peatfield et al.
8,597,274 B2 12/2013 Sloan et al.
8,622,988 B2 1/2014 Hayter
8,701,264 B2 4/2014 Martinson
8,727,117 B2 5/2014 Maasarani
8,765,482 B2 7/2014 Joseph et al.
8,810,394 B2 8/2014 Kalpin
8,894,262 B2 11/2014 Celentano et al.
9,005,166 B2 4/2015 Uber, III et al.
9,061,097 B2 6/2015 Holt et al.
9,171,343 B1 10/2015 Fischell et al.
9,211,065 B2 12/2015 Marsh et al.
9,233,204 B2 1/2016 Booth et al.
9,248,229 B2 2/2016 Devouassoux et al.
9,265,877 B2 2/2016 McArthur et al.
9,427,710 B2 8/2016 Jansen
9,486,571 B2 11/2016 Rosinko
9,572,926 B2 2/2017 Cabiri
9,579,456 B2 2/2017 Budiman et al.
9,598,195 B2 3/2017 Deutschle et al.
9,743,224 B2 8/2017 San Vicente et al.
9,814,832 B2 11/2017 Agard et al.
9,862,519 B2 1/2018 Deutschle et al.
9,907,515 B2 3/2018 Doyle, III et al.
9,980,140 B1 5/2018 Spencer et al.
9,984,773 B2 5/2018 Gondhalekar et al.
10,046,114 B1 8/2018 Biederman et al.
RE47,100 E 10/2018 Smith et al.
10,086,131 B2 10/2018 Okihara
10,248,839 B2 4/2019 Levy et al.
10,252,002 B2 4/2019 Haider et al.
10,335,464 B1 7/2019 Michelich et al.
10,342,926 B2 7/2019 Nazzaro et al.
10,441,717 B2 10/2019 Schmid et al.
10,522,252 B2 * 12/2019 Vanderveen ........... G06Q 50/00
10,583,250 B2 3/2020 Mazlish et al.
10,661,012 B2 5/2020 Nazzaro et al.
10,737,024 B2 8/2020 Schmid
10,987,468 B2 4/2021 Mazlish et al.
11,197,964 B2 12/2021 Sjolund et al.
11,260,169 B2 3/2022 Estes
2001/0021803 A1 9/2001 Blank et al.
2001/0034023 A1 10/2001 Stanton, Jr. et al.
2001/0034502 A1 10/2001 Moberg et al.
2001/0051377 A1 12/2001 Hammer et al.
2001/0053895 A1 12/2001 Vaillancourt
2002/0010401 A1 1/2002 Bushmakin et al.
2002/0010423 A1 1/2002 Gross et al.
2002/0016568 A1 2/2002 Lebel et al.
2002/0032374 A1 3/2002 Holker et al.
2002/0040208 A1 4/2002 Flaherty et al.
2002/0123740 A1 9/2002 Flaherty et al.
2002/0128543 A1 9/2002 Leonhardt
2002/0147423 A1 10/2002 Burbank et al.
2002/0155425 A1 10/2002 Han et al.
2002/0161288 A1 10/2002 Shin et al.
2002/0161307 A1 10/2002 Yu et al.
2003/0023148 A1 1/2003 Lorenz et al.
2003/0050621 A1 3/2003 Lebel et al.
2003/0060692 A1 3/2003 Ruchti et al.
2003/0073952 A1 4/2003 Flaherty et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0130616 A1 7/2003 Steil et al.
2003/0135388 A1 7/2003 Martucci et al.
2003/0144582 A1 7/2003 Cohen et al.
2003/0163097 A1 8/2003 Fleury et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2004/0010207 A1 1/2004 Flaherty et al.
2004/0010507 A1 1/2004 Bellew
2004/0034295 A1 2/2004 Salganicoff
2004/0045879 A1 3/2004 Shults et al.
2004/0051368 A1 3/2004 Caputo et al.
2004/0064259 A1 4/2004 Haaland et al.
2004/0085215 A1 5/2004 Moberg et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0009126 A1 1/2005 Andrews et al.
2005/0020980 A1 1/2005 Noue et al.
2005/0022274 A1 1/2005 Campbell et al.
2005/0033148 A1 2/2005 Haueter et al.
2005/0049179 A1 3/2005 Davidson et al.
2005/0055242 A1 3/2005 Bello et al.
2005/0065464 A1 3/2005 Talbot et al.
2005/0065465 A1 3/2005 Ebel et al.
2005/0075624 A1 4/2005 Miesel
2005/0105095 A1 5/2005 Pesach et al.
2005/0125162 A1 6/2005 Hajizadeh et al.
2005/0137573 A1 6/2005 Mclaughlin
2005/0171503 A1 8/2005 Van Den Berghe et al.
2005/0182306 A1 8/2005 Sloan
2005/0192494 A1 9/2005 Ginsberg
2005/0192557 A1 9/2005 Brauker et al.
2005/0197621 A1 9/2005 Poulsen et al.
2005/0201897 A1 9/2005 Zimmer et al.
2005/0203360 A1 9/2005 Brauker et al.
2005/0203461 A1 9/2005 Flaherty et al.
2005/0232815 A1 10/2005 Ruhl et al.
2005/0238507 A1 10/2005 Dilanni et al.
2005/0261660 A1 11/2005 Choi
2005/0272640 A1 12/2005 Doyle et al.
2005/0277164 A1 12/2005 Drucker et al.
2005/0277912 A1 12/2005 John
2006/0009727 A1 1/2006 OMahony et al.
2006/0079809 A1 4/2006 Goldberger et al.
2006/0086909 A1 4/2006 Schaber
2006/0092569 A1 5/2006 Che et al.
2006/0100494 A1 5/2006 Kroll
2006/0134323 A1 6/2006 OBrien
2006/0167350 A1 7/2006 Monfre et al.
2006/0173406 A1 8/2006 Hayes et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.

(56) References Cited

U.S. PATENT DOCUMENTS

2006/0264895 A1 11/2006 Flanders
2006/0264926 A1 11/2006 Kochamba
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0027370 A1 2/2007 Brauker et al.
2007/0060796 A1 3/2007 Kim
2007/0060869 A1 3/2007 Tolle et al.
2007/0060872 A1 3/2007 Hall et al.
2007/0078784 A1 4/2007 Donovan et al.
2007/0083160 A1 4/2007 Hall et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0173761 A1 7/2007 Kanderian et al.
2007/0173974 A1 7/2007 Lin et al.
2007/0179352 A1 8/2007 Randlov et al.
2007/0179885 A1 8/2007 Bird et al.
2007/0191716 A1 8/2007 Goldberger et al.
2007/0191770 A1 8/2007 Moberg et al.
2007/0197163 A1 8/2007 Robertson
2007/0225675 A1 9/2007 Robinson et al.
2007/0233051 A1 10/2007 Hohl et al.
2007/0244381 A1 10/2007 Robinson et al.
2007/0249007 A1 10/2007 Rosero
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0004515 A1 1/2008 Jennewine
2008/0027371 A1 1/2008 Higuchi et al.
2008/0033272 A1 2/2008 Gough et al.
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0077081 A1 3/2008 Mounce et al.
2008/0078400 A1 4/2008 Martens et al.
2008/0097289 A1 4/2008 Steil et al.
2008/0132880 A1 6/2008 Buchman
2008/0161664 A1 7/2008 Mastrototaro et al.
2008/0172026 A1 7/2008 Blomquist
2008/0173073 A1 7/2008 Downie et al.
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0255438 A1 10/2008 Saidara et al.
2008/0269585 A1 10/2008 Ginsberg
2008/0269714 A1 10/2008 Mastrototaro et al.
2008/0269723 A1 10/2008 Mastrototaro et al.
2008/0281290 A1 11/2008 Yodfat et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0048556 A1 2/2009 Durand
2009/0054753 A1 2/2009 Robinson et al.
2009/0062767 A1 3/2009 Van Antwerp et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0112769 A1 4/2009 Dicks et al.
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0177142 A1 7/2009 Blomquist et al.
2009/0198350 A1 8/2009 Thiele
2009/0204078 A1 8/2009 Mitchell et al.
2009/0221890 A1 9/2009 Saffer et al.
2009/0228214 A1 9/2009 Say et al.
2009/0254041 A1 10/2009 Krag et al.
2009/0282947 A1 11/2009 Powell
2009/0318791 A1 12/2009 Kaastrup
2009/0326343 A1 12/2009 Gable et al.
2010/0057042 A1 3/2010 Hayter
2010/0076275 A1 3/2010 Chu et al.
2010/0094251 A1 4/2010 Estes
2010/0114026 A1 5/2010 Karratt et al.
2010/0121170 A1 5/2010 Rule
2010/0137784 A1 6/2010 Cefai et al.
2010/0145272 A1 6/2010 Cefai et al.
2010/0152658 A1 6/2010 Hanson et al.
2010/0168683 A1 7/2010 Cabiri
2010/0174228 A1 7/2010 Buckingham et al.
2010/0185175 A1 7/2010 Kamen et al.
2010/0211003 A1 8/2010 Sundar et al.
2010/0228110 A1 9/2010 Tsoukalis
2010/0262117 A1 10/2010 Magni et al.
2010/0262434 A1 10/2010 Shaya
2010/0286997 A1 11/2010 Srinivasan
2010/0295686 A1 11/2010 Sloan et al.
2010/0298765 A1 11/2010 Budiman et al.
2010/0317951 A1 12/2010 Rutkowski et al.
2011/0021584 A1 1/2011 Berggren et al.
2011/0028817 A1 2/2011 Jin et al.
2011/0054390 A1 3/2011 Searle et al.
2011/0054399 A1 3/2011 Chong et al.
2011/0071765 A1 3/2011 Yodfat et al.
2011/0124996 A1 5/2011 Reinke et al.
2011/0142688 A1 6/2011 Chappel et al.
2011/0144586 A1 6/2011 Michaud et al.
2011/0152658 A1 6/2011 Peyser et al.
2011/0160652 A1 6/2011 Yodfat et al.
2011/0178472 A1 7/2011 Cabiri
2011/0190694 A1 8/2011 Lanier, Jr. et al.
2011/0193704 A1 8/2011 Harper et al.
2011/0202005 A1 8/2011 Yodfat et al.
2011/0213306 A1 9/2011 Hanson et al.
2011/0218495 A1 9/2011 Remde
2011/0225024 A1 9/2011 Seyer et al.
2011/0230833 A1 9/2011 Landman et al.
2011/0246235 A1 10/2011 Powell et al.
2011/0251509 A1 10/2011 Beyhan et al.
2011/0289497 A1 11/2011 Kiaie et al.
2011/0313680 A1 12/2011 Doyle, III
2011/0316562 A1 12/2011 Cefai et al.
2012/0003935 A1 1/2012 Lydon et al.
2012/0010594 A1 1/2012 Holt et al.
2012/0029941 A1 2/2012 Malave et al.
2012/0030393 A1 2/2012 Ganesh et al.
2012/0050046 A1 3/2012 Satorius et al.
2012/0053556 A1 3/2012 Lee
2012/0054841 A1 3/2012 Schultz et al.
2012/0078067 A1 3/2012 Kovatchev et al.
2012/0078161 A1 3/2012 Masterson et al.
2012/0078181 A1 3/2012 Smith et al.
2012/0095316 A1 4/2012 Lewis et al.
2012/0101451 A1 4/2012 Boit et al.
2012/0123234 A1 5/2012 Atlas et al.
2012/0136336 A1 5/2012 Mastrototaro et al.
2012/0153936 A1 6/2012 Romani et al.
2012/0182939 A1 7/2012 Rajan et al.
2012/0184909 A1 7/2012 Gyrn
2012/0190955 A1 7/2012 Rao et al.
2012/0201048 A1 8/2012 Prais
2012/0203085 A1 8/2012 Rebec
2012/0203178 A1 8/2012 Tverskoy
2012/0205441 A1* 8/2012 Utech ................ G06Q 10/0833
235/376
2012/0215087 A1 8/2012 Cobelli et al.

(56) References Cited

U.S. PATENT DOCUMENTS

2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0265166 A1 10/2012 Yodfat
2012/0271655 A1 10/2012 Knobel et al.
2012/0277667 A1 11/2012 Yodat et al.
2012/0277668 A1 11/2012 Chawla
2012/0282111 A1 11/2012 Nip et al.
2012/0295550 A1 11/2012 Wilson et al.
2013/0030358 A1 1/2013 Yodfat et al.
2013/0030841 A1 1/2013 Bergstrom et al.
2013/0036100 A1 2/2013 Nagpal et al.
2013/0060194 A1 3/2013 Rostein
2013/0080832 A1 3/2013 Dean et al.
2013/0138452 A1 5/2013 Cork et al.
2013/0158503 A1 6/2013 Kanderian, Jr. et al.
2013/0173473 A1 7/2013 Birtwhistle et al.
2013/0178791 A1 7/2013 Javitt
2013/0204130 A1 8/2013 Mcarthur et al.
2013/0231642 A1 9/2013 Doyle et al.
2013/0245545 A1 9/2013 Arnold et al.
2013/0253472 A1 9/2013 Cabiri
2013/0261406 A1 10/2013 Rebec et al.
2013/0274576 A1 10/2013 Amirouche et al.
2013/0296823 A1 11/2013 Melker et al.
2013/0317753 A1 11/2013 Kamen et al.
2013/0338576 A1 12/2013 OConnor et al.
2014/0005633 A1 1/2014 Finan
2014/0012119 A1 1/2014 Geaghan et al.
2014/0054883 A1 2/2014 Lanigan et al.
2014/0066886 A1 3/2014 Roy et al.
2014/0074033 A1 3/2014 Sonderegger et al.
2014/0078263 A1 3/2014 Kim
2014/0114277 A1 4/2014 Eggert et al.
2014/0121635 A1 5/2014 Hayter
2014/0128839 A1 5/2014 Dilanni et al.
2014/0131199 A1 5/2014 Simmons et al.
2014/0135880 A1 5/2014 Baumgartner et al.
2014/0146202 A1 5/2014 Boss et al.
2014/0148784 A1 5/2014 Anderson et al.
2014/0163664 A1 6/2014 Goldsmith
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0254170 A1 9/2014 Celentano et al.
2014/0276554 A1 9/2014 Finan et al.
2014/0276556 A1 9/2014 Saint et al.
2014/0278123 A1 9/2014 Prodhom et al.
2014/0296787 A1 10/2014 Agard et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0038898 A1 2/2015 Palmer et al.
2015/0057913 A1 2/2015 Benhammou
2015/0119666 A1 4/2015 Brister et al.
2015/0120317 A1 4/2015 Mayou et al.
2015/0134265 A1 5/2015 Kohlbrecher et al.
2015/0165119 A1 6/2015 Palerm et al.
2015/0173674 A1 6/2015 Hayes et al.
2015/0213217 A1 7/2015 Amarasingham et al.
2015/0217052 A1 8/2015 Keenan et al.
2015/0217053 A1 8/2015 Booth et al.
2015/0265767 A1 9/2015 Vazquez et al.
2015/0283335 A1 10/2015 Lin
2015/0290391 A1 10/2015 Schmid et al.
2015/0306314 A1 10/2015 Doyle et al.
2015/0338349 A1 11/2015 Carter et al.
2015/0351671 A1 12/2015 Vanslyke et al.
2015/0356255 A1* 12/2015 Simpson ................ G16H 10/60
705/3
2015/0361154 A1 12/2015 Jowett et al.
2015/0366945 A1 12/2015 Greene
2016/0015891 A1 1/2016 Papiorek
2016/0022905 A1 1/2016 Nagar et al.
2016/0038673 A1 2/2016 Morales
2016/0038689 A1 2/2016 Lee et al.
2016/0051749 A1 2/2016 Istoc
2016/0058941 A1 3/2016 Wu et al.
2016/0082187 A1 3/2016 Schaible et al.
2016/0089494 A1 3/2016 Guerrini
2016/0135747 A1 5/2016 Frey et al.
2016/0175520 A1 6/2016 Palerm et al.
2016/0184517 A1 6/2016 Baek et al.
2016/0228641 A1 8/2016 Gescheit et al.
2016/0243318 A1 8/2016 Despa et al.
2016/0256087 A1 9/2016 Doyle et al.
2016/0287512 A1 10/2016 Cooper et al.
2016/0302054 A1 10/2016 Kimura et al.
2016/0310665 A1 10/2016 Hwang et al.
2016/0331310 A1 11/2016 Kovatchev
2016/0339172 A1 11/2016 Michaud et al.
2016/0354543 A1 12/2016 Cinar et al.
2017/0028132 A1 2/2017 Cronenberg et al.
2017/0049386 A1 2/2017 Abraham et al.
2017/0106138 A1 4/2017 Cabiri
2017/0143899 A1 5/2017 Gondhalekar et al.
2017/0143900 A1 5/2017 Rioux et al.
2017/0156682 A1 6/2017 Doyle et al.
2017/0173261 A1 6/2017 O'Connor et al.
2017/0189270 A1 7/2017 Nazzaro et al.
2017/0189625 A1 7/2017 Cirillo et al.
2017/0214584 A1 7/2017 Kanojia et al.
2017/0234858 A1 8/2017 Depa et al.
2017/0281877 A1 10/2017 Marlin et al.
2017/0296746 A1 10/2017 Chen et al.
2017/0311903 A1 11/2017 Davis et al.
2017/0348479 A1 12/2017 Choate et al.
2017/0348482 A1 12/2017 Duke et al.
2017/0354785 A1 12/2017 Gazeley et al.
2018/0015274 A1 1/2018 Haury et al.
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 O'Connor et al.
2018/0126073 A1 5/2018 Wu et al.
2018/0169334 A1 6/2018 Grosman et al.
2018/0200434 A1 7/2018 Mazlish et al.
2018/0200438 A1 7/2018 Mazlish et al.
2018/0200441 A1 7/2018 Desborough et al.
2018/0204636 A1 7/2018 Edwards et al.
2018/0207357 A1 7/2018 John
2018/0236173 A1 8/2018 McCaffrey et al.
2018/0256815 A1 9/2018 Nazzaro
2018/0277253 A1 9/2018 Gondhalekar et al.
2018/0280609 A1 10/2018 Nishimura et al.
2018/0289891 A1 10/2018 Finan et al.
2018/0296757 A1 10/2018 Finan et al.
2018/0307515 A1 10/2018 Meller et al.
2018/0342317 A1 11/2018 Skirble et al.
2018/0369479 A1 12/2018 Hayter et al.
2019/0022317 A1 1/2019 Uddin et al.
2019/0076600 A1 3/2019 Grosman et al.
2019/0091404 A1 3/2019 Nazzaro et al.
2019/0132801 A1 5/2019 Kamath et al.
2019/0167895 A1 6/2019 Dechellette et al.
2019/0240403 A1 8/2019 Palerm et al.
2019/0240417 A1 8/2019 Hostettler et al.
2019/0290844 A1 9/2019 Monirabbasi et al.
2019/0321545 A1 10/2019 Saint
2019/0336683 A1 11/2019 O'Connor et al.
2019/0336684 A1 11/2019 O'Connor et al.
2019/0348157 A1 11/2019 Booth et al.
2020/0046268 A1 2/2020 Patek et al.
2020/0101222 A1 4/2020 Lintereur et al.
2020/0101223 A1 4/2020 Lintereur et al.

(56) References Cited

U.S. PATENT DOCUMENTS

| | | | |
|---|---|---|---|
| 2020/0101225 | A1 | 4/2020 | O'Connor et al. |
| 2020/0197605 | A1 | 6/2020 | Haidar |
| 2020/0219625 | A1 | 7/2020 | Kahlbaugh |
| 2020/0261643 | A1 | 8/2020 | Boyaval et al. |
| 2020/0342974 | A1 | 10/2020 | Chen et al. |
| 2020/0365240 | A1 | 11/2020 | Chen et al. |
| 2021/0050085 | A1 | 2/2021 | Hayter et al. |
| 2021/0098105 | A1 | 4/2021 | Lee et al. |
| 2022/0023536 | A1 | 1/2022 | Graham et al. |

FOREIGN PATENT DOCUMENTS

| | | | |
|---|---|---|---|
| CA | 2863379 | A1 | 8/2013 |
| CN | 1297140 | A | 5/2001 |
| CN | 201134101 | Y | 10/2008 |
| DE | 19756872 | A1 | 7/1999 |
| EP | 0341049 | A2 | 11/1989 |
| EP | 0496305 | A2 | 7/1992 |
| EP | 0549341 | A1 | 6/1993 |
| EP | 1491144 | A1 | 12/2004 |
| EP | 0801578 | B1 | 7/2006 |
| EP | 1762263 | A1 | 3/2007 |
| EP | 1839694 | A1 | 10/2007 |
| EP | 1852703 | A1 | 11/2007 |
| EP | 2099384 | A1 | 9/2009 |
| EP | 2139382 | A1 | 1/2010 |
| EP | 2353628 | A2 | 8/2011 |
| EP | 2397181 | A1 | 12/2011 |
| EP | 2666520 | A1 | 11/2013 |
| EP | 2695573 | A2 | 2/2014 |
| EP | 1874390 | B1 | 10/2014 |
| EP | 2830499 | A1 | 2/2015 |
| EP | 2943149 | A1 | 11/2015 |
| EP | 3068290 | A1 | 9/2016 |
| EP | 3135965 | A1 | 3/2017 |
| EP | 3177344 | A1 | 6/2017 |
| EP | 3187201 | A1 | 7/2017 |
| EP | 3314548 | A1 | 5/2018 |
| EP | 3000497 | A1 | 1/2019 |
| EP | 1571582 | B1 | 4/2019 |
| EP | 2897071 | B1 | 5/2019 |
| EP | 3598942 | A1 | 1/2020 |
| EP | 3607985 | A1 | 2/2020 |
| ES | 2559866 | T3 | 2/2016 |
| FR | 2096275 | A5 | 2/1972 |
| GB | 357139 | A | 9/1931 |
| GB | 810488 | A | 3/1959 |
| GB | 1401588 | A | 7/1975 |
| GB | 2176595 | A | 12/1986 |
| GB | 2443260 | A | 4/2008 |
| GB | 2443261 | A | 4/2008 |
| GB | 2461086 | A | 12/2009 |
| GB | 2495014 | A | 3/2013 |
| GB | 2524717 | A | 10/2015 |
| GB | 2525149 | A | 10/2015 |
| JP | 51125993 | A | 11/1976 |
| JP | 02131777 | A | 5/1990 |
| JP | 2001190659 | A | 7/2001 |
| JP | 2003154190 | A | 5/2003 |
| JP | 2007144141 | A1 | 6/2007 |
| JP | 2004283378 | A | 10/2007 |
| JP | 2007307359 | A | 11/2007 |
| JP | 2008242502 | A | 10/2008 |
| JP | 2009523535 | A | 6/2009 |
| JP | 2012210441 | A | 11/2012 |
| JP | 2017525451 | A | 9/2017 |
| JP | 2018153569 | A | 10/2018 |
| JP | 2019525276 | A | 9/2019 |
| NO | 9819145 | A1 | 5/1998 |
| NO | 2008024814 | A2 | 2/2008 |
| NO | 2012177353 | A1 | 12/2012 |
| TW | 200740148 | A | 10/2007 |
| TW | M452390 | U | 5/2013 |
| WO | 9800193 | A1 | 1/1998 |
| WO | 9801071 | A1 | 1/1998 |
| WO | 9824495 | A1 | 6/1998 |
| WO | 9841267 | A1 | 9/1998 |
| WO | 9956803 | A1 | 11/1999 |
| WO | 0010628 | A2 | 3/2000 |
| WO | 0013580 | A1 | 3/2000 |
| WO | 0019887 | A1 | 4/2000 |
| WO | 0030705 | A1 | 6/2000 |
| WO | 200032258 | A1 | 6/2000 |
| WO | 0061215 | A1 | 10/2000 |
| WO | 0078210 | A1 | 12/2000 |
| WO | 0172354 | A2 | 10/2001 |
| WO | 2002015954 | A1 | 2/2002 |
| WO | 2002043866 | A2 | 6/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2004043250 | A1 | 5/2004 |
| WO | 2005110601 | A1 | 5/2004 |
| WO | 2004092715 | A1 | 10/2004 |
| WO | 2005031631 | A2 | 4/2005 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2006060668 | A2 | 6/2006 |
| WO | 2007064835 | A2 | 6/2007 |
| WO | 2007078937 | A1 | 7/2007 |
| WO | 2007084214 | A1 | 7/2007 |
| WO | 2007092618 | A2 | 8/2007 |
| WO | 2007112034 | A2 | 10/2007 |
| WO | 2008024810 | A2 | 2/2008 |
| WO | 2008029403 | A1 | 3/2008 |
| WO | 2008133702 | A1 | 11/2008 |
| WO | 2009023634 | A2 | 2/2009 |
| WO | 2009032399 | A1 | 3/2009 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010025433 | A1 | 3/2010 |
| WO | 2010053702 | A1 | 5/2010 |
| WO | 2010078434 | A2 | 7/2010 |
| WO | 2010132077 | A1 | 11/2010 |
| WO | 2010138848 | A1 | 12/2010 |
| WO | 2010146579 | A1 | 12/2010 |
| WO | 2010147659 | A2 | 12/2010 |
| WO | 2011012465 | A1 | 2/2011 |
| WO | 2011095483 | A1 | 8/2011 |
| WO | 2011133823 | A1 | 10/2011 |
| WO | 2012045667 | A2 | 4/2012 |
| WO | 2012108959 | A1 | 8/2012 |
| WO | 2012134588 | A1 | 10/2012 |
| WO | 2012178134 | A2 | 12/2012 |
| WO | 2013078200 | A1 | 5/2013 |
| WO | 2013134486 | A2 | 9/2013 |
| WO | 2013149186 | A1 | 10/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014136105 | A1 | 9/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2015187793 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2016181384 | A2 | 11/2016 |

(56) References Cited

FOREIGN PATENT DOCUMENTS

| | | |
|---|---|---|
| WO | 2017004278 A1 | 1/2017 |
| WO | 2017089289 A1 | 6/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019043702 A1 | 3/2019 |
| WO | 2019077482 A1 | 4/2019 |
| WO | 2019094440 A1 | 5/2019 |
| WO | 2019195521 A1 | 10/2019 |
| WO | 2019213493 A1 | 11/2019 |
| WO | 2019246381 A1 | 12/2019 |
| WO | 2020081393 A1 | 4/2020 |
| WO | 2020124058 A1 | 6/2020 |
| WO | 2021011738 A1 | 1/2021 |

OTHER PUBLICATIONS

Jiang, Duo, et al. "Hierarchical cloud-fog platform for communication in disaster incident coordination." IEEE Mobile Cloud (2019). (Year: 2019).*

International Search Report and Written Opinion for the International Patent Application No. PCT/US2021/047690, mailed Jan. 14, 2022, 13 pages.

International Search Report and Written Opinion for the International Patent Application No. PCT/US2022/055745, mailed Feb. 14, 2022, 13 pages.

International Search Report and Written Opinion for the International Patent Application No. PCT/US2021/053162, mailed Mar. 28, 2022, 18 pages.

International Search Report and Written Opinion for the International Patent Application No. PCT/US2021/064041, mailed Apr. 29, 2022, 11 pages.

International Search Report and Written Opinion for the International Patent Application No. PCT/US2022/015809, mailed Jun. 20, 2022, 15 pages.

International Search Report and Written Opinion for International Patent Application No. PCT/US2022/029012, mailed Aug. 19, 2022, 12 pages.

"eHEALTH; Architecture; Analysis of user service models, technologies and applications supporting eHealth", Technical Report, European Telecommunications Standards Institute (ETSI), 650, Route Des Lucioles; F-06921 Sophia-Antipolis; France, vol. tr_102764v010101p.pdf, No. VI.1.1, Feb. 1, 2009 (Feb. 1, 2009).

International Preliminary Report on Patentability for the International Patent Application No. PCT/US2019/042160, mailed Jan. 28, 2021, 12 pages.

International Search Report and Written Opinion for the International Patent Application No. PCT/US2021/047695, mailed Jan. 31, 2022, 26 pages.

International Search Report and Written Opinion for the International Patent Application No. PCT/US21/064056, mailed Apr. 4, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.

International Search Report and Written Opinion for the International Patent Application No. PCT/US22/018700, mailed Jun. 7, 2022, 13 pages.

Legacy Med Search, Insulet Enrolls First Patients in Clinical Trial for Omnipod, Sep. 16, 2016, available at URL: https://legacymedsearch.com/insulet-enrolls-first-patients-in-clinical-trial-for-omnipod-artificial-pancreas-system/.

"eHEALTH; Architecture; Analysis of user service models, technologies and applications supporting eHealth", Technical Report, European Telecommunications Standards Institute (ETSI), 650, Route Des Lucioles ; F-06921 Sophia-Antipolis ; France, vol. tr_102764v010101p.pdf, No. V1.1.1, Feb. 1, 2009 (Feb. 1, 2009).

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The Nice-Sugar (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et. al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

(56) References Cited

OTHER PUBLICATIONS

Finkielman et al., "Agreement Between Bedside Blood and Plasma Glucose Measurement in the ICU Setting"; retrieved from http://www.chestjournal.org; Chest/127/5/May 2005.
Glucon Critical Care Blood Glucose Monitor, Glucon; retrieved on Dec. 29, 2010 from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech, vol. Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
Anonymous: "Fuzzy control system", Wikipedia, Jan. 10, 2020. URL: https://en.wikipedia.org/w/index.php? title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al.: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
European Search Report for the European Patent Application No. EP03743667, dated Jul. 22, 2008.
International Search Report and Written Opinion mailed Sep. 9, 2016, issued in PCT Patent Application No. PCT/US2016/037189, 12 pages.
Preliminary Report on Patentability mailed Dec. 21, 2017, issued in PCT Patent Application No. PCT/US2016/037189.
U.K. Intellectual Property Office, GB Application No. GB 1401587. 9, "Search Report under Section 17(5)" Aug. 11, 2015, 1 page.
International Search Report and Written Opinion for PCT Application No. PCT/GB2015/050247, May 8, 2015, 14 pages.
Extended Search Report mailed Nov. 24, 2017, issued in European Patent Application No. 15779465.2, 10 pages.
International Search Report and Written Opinion for PCT Application No. PCT/US15/26875, mailed Jan. 18, 2016, 10 pages.
U.K. Intellectual Property Office, GB Application No. GB 1401588. 7, "Search Report under Section 17(5)" Aug. 17, 2015, 1 page.
U.K. Intellectual Property Office, GB Application No. GB 1401589. 5, "Search Report under Section 17" Jul. 27, 2015, 1 page.
International Search Report and Written Opinion for PCT Application No. PCT/GB2015/050250, May 7, 2015, 9 pages.
3GPP TS 23.003 V10.0.0.0 Numbering, addressing and identification. Dec. 2010.
International Search Report and Written Opinion for PCT Application No. PCT/GB2015/050251, Jun. 12, 2015, 9 bages.
European Search Report for the European Patent Application No. EP19194241, dated Oct. 22, 2019, 6 pages.
International Preliminary Report on Patentability for PCT/US2017/061095, issued on May 14, 2019, 6 pages.
International Search Report and Written Opinion for PCT/US18/52468, mailed on Feb. 26, 2019, 16 pages.
International Search Report and Written Opinion for PCT/US2017/061095, mailed on Feb. 20, 2018, 8 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.

(56) References Cited

OTHER PUBLICATIONS

International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column line 16- line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116—line 118, line 439—line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on IOS 11", GoToTags, Sep. 11, 2017, web <https://gototags.com/blog/read-hfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.

(56) References Cited

OTHER PUBLICATIONS

International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 bages.
Joao C. Silva et al: "Context-awareness for mobility management: A systems survey for healthcare monitoring", Broadband and Biomedical Communications (IB2COM), 2011 6TH International Conference On IEEE, Nov. 21, 2011 (Nov. 21, 2011), pp. 18-23.

* cited by examiner

FIG. 3
Cloud-Based Services
111
MDA
129
Device Updates
310
Supply Ordering
312
Prescription Control
314
Physician Data Sharing
316
Training Validation
318
Caretaker Data Sharing
320
Region-Based Functionalities
322
Data Persistence
324
Long-Term User Insights
326
Big Data Adaptivity
328
Inter-Component Communication
330

AUTOMATIC DRUG DELIVERY SYSTEM HAVING MULTIPLE COMMUNICATION OPTIONS

RELATED APPLICATIONS

This application claims the benefit of U.S. Provisional Patent Application No. 63/325,867, filed Mar. 31, 2022, the contents of which are incorporated herein by reference in their entirety.

BACKGROUND

Many conventional automated drug delivery systems are well known, including, for example, wearable drug delivery devices. The drug delivery device can be designed to deliver any type of liquid drug to a user. In specific embodiments, the drug delivery device can be, for example, an OmniPod® drug delivery device manufactured by Insulet Corporation of Acton, Massachusetts. The drug delivery device can be a drug delivery device such as those described in U.S. Pat. Nos. 7,303,549, 7,137,964, or U.S. Pat. No. 6,740,059, each of which is incorporated herein by reference in its entirety.

It is common for automated drug delivery systems to comprise a plurality of components, with each component contributing to the overall functionality of the system. For example, an automated drug delivery system may include a wearable drug delivery device, a wearable blood glucose sensor, a user device, for example, a smartphone, and/or an accessory device, for example, a smartwatch. In some instances, a medication delivery algorithm may execute on the wearable drug delivery device, may execute on the user device, or may have its functionality split between multiple components of the system. In addition, the medication delivery algorithm may require data from one or more sensors. As such, safe and proper operation of the system requires reliable communication between the various components.

Typically, the components comprising the automated drug delivery system communicate with each other via a preferred method and not limited to, for example, Bluetooth®. However, it is possible, under some circumstances, that the components may be prevented from communicating with each other via a Bluetooth connection. For example, it is not uncommon for a user, when at home, to not carry a smartphone or any controller which can interact with drug delivery system for bolus or for querying status of the system or any related activity, at all times. As such, is possible that the smartphone and the drug delivery device will be out of Bluetooth communications range with each other. In addition, Bluetooth communications may sometimes be interrupted by interference. For example, if a wearable sensor and a drug delivery device are worn on opposite sides of the user's body, the user's body may interfere with the Bluetooth connection. If the drug delivery device is operating under control of a user device running all or a part of a medication delivery algorithm, or if the drug delivery device is not able to receive sensor readings, the communication difficulties may cause a dangerous situation for the user.

In addition, the automated drug delivery system may be operable to be able to receive cloud-based services. For example, the medication delivery algorithm could be run (in whole or in part) on a cloud server and may control the drug delivery device remotely. Typically, the only component of the automated drug delivery system able to communicate with cloud-based services is the user device 105 (e.g., a smartphone), which may communicate via a Wi-Fi connection or a cellular connection. However, as previously mentioned, there are instances wherein the user device is unable to communicate with other components of the system.

Therefore, it would be desirable to provide other components of the automated drug delivery system with options for communicating either with each other, or with another entity such as a cloud server to receive cloud-based services directly.

Definitions

As used herein, the term "liquid drug" should be interpreted to include any drug in liquid form capable of being administered by a drug delivery device via a subcutaneous cannula, including, for example, insulin, GLP-1, pramlintide, glucagon, morphine, blood pressure medicines, chemotherapy drugs, fertility drugs, or the like, or co-formulations of two or more of GLP-1, pramlintide, and insulin.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In an embodiment, various components of the system may be provided with various modes of communication such as to enable communication with other components of the system and with cloud-based services. For example, in situations wherein Bluetooth communications are not possible between a drug delivery device and a user device, such as when the drug delivery device and the user device are out of Bluetooth communications range, the drug delivery device may be provided with Wi-Fi capabilities, allowing the drug delivery device to join a local Wi-Fi network and communicate with the user device via the network, or, alternatively, to allow the drug delivery device to establish a peer-to-peer Wi-Fi connection and to communicate with the user device directly.

Additionally, it may be desirable for a drug delivery device, or other components of the system, to receive cloud-based services directly from a cloud server instead of receiving the cloud-based services via the user device. It is also possible that the components of the system may not be able to communicate with a cloud server via Wi-Fi because, for example, the Wi-Fi signal may be weak or the components may be out of range of a Wi-Fi hotspot. In such cases, components may be provided with a cellular radio, which may include an activated SIM card, or be capable of receiving an eSIM card, and may have the ability to establish a cellular data connection with each other (either directly or via a cloud server) or with a cloud server such as to be able to receive cloud-based services directly from the cloud server via the cellular data connection.

BRIEF DESCRIPTION OF THE DRAWINGS

In the drawings, like reference characters generally refer to the same parts throughout the different views. In the following description, various embodiments are described with reference to the following drawings, in which.

DETAILED DESCRIPTION

This disclosure presents various systems, components, and methods for moving a liquid drug from a liquid reservoir in a drug delivery device to a patient interface, such as a needle or cannula. The embodiments described herein provide one or more advantages over conventional, prior art systems, components, and methods, namely, a smaller overall footprint of the drug delivery device.

Various embodiments include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be carried by the user or worn on the body of the user and that executes an algorithm that computes the times and dosages of delivery of the medication.

For example, the user device may execute an "artificial-pancreas" (AP) algorithm that computes the times and dosages of delivery of insulin. The user device may also be in communication with a sensor, such as a glucose sensor or a continuous glucose monitor (CGM), that collects data on a physical attribute or condition of the user, such as a glucose level. The sensor may be disposed in or on the body of the user and may be part of the drug delivery device or may be a separate device.

Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the drug delivery device contains computing hardware (e.g., a processor, memory, firmware, etc.) that executes some or all of the algorithm that computes the times and dosages of delivery of the medication.

Figure 1:
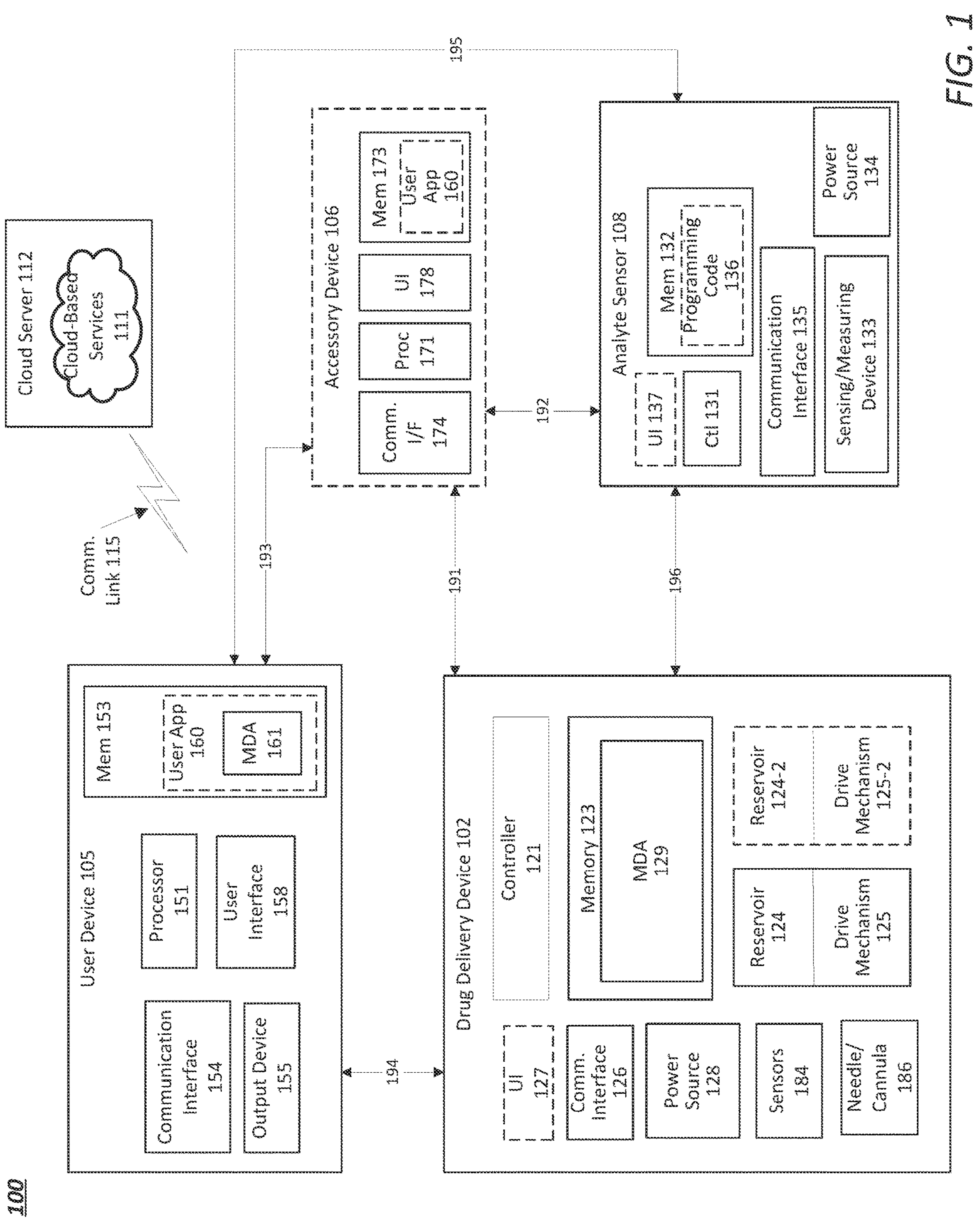
FIG. 1 illustrates a functional block diagram of an exemplary system suitable for implementing the systems and methods disclosed herein.

FIG. 1 illustrates a functional block diagram of an exemplary drug delivery system 100 suitable for implementing the systems and methods described herein. The drug delivery system 100 may implement (and/or provide functionality for) a medication delivery algorithm, such as an artificial pancreas (AP) application, to govern or control the automated delivery of a drug or medication, such as insulin, to a user (e.g., to maintain euglycemia—a normal level of glucose in the blood). The drug delivery system 100 may be an automated drug delivery system that may include a drug delivery device 102 (which may be wearable), an analyte sensor 108 (which may also be wearable), and a user device 105.

Drug delivery system 100, in an optional example, may also include an accessory device 106, such as a smartwatch, a personal assistant device, an insulin smartpen, or the like, which may communicate with the other components of system 100 via either a wired or wireless communication links 191-193.

User Device

The user device 105 may be a computing device such as a smartphone, a smartwatch, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 incorporating MDA 161 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to activate, deactivate, trigger a needle/canula insertion, program, adjust settings, and/or control operation of drug delivery device 102 and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 includes MDA 161, the processor 151 is also configured to execute a diabetes treatment plan (which may be stored in a memory) that is managed by user app 160. In addition to the functions mentioned above, when user app 160 is an AP application, it may further provide functionality to determine a carbohydrate-compensation dosage, a correction bolus dosage and determine a real-time basal dosage according to a diabetes treatment plan. In addition, user app 160 provides functionality to output signals to the drug delivery device 102 via communications interface 154 to deliver the determined bolus and/or basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

Drug Delivery Device

In various exemplary embodiments, drug delivery device 102 may include a reservoir 124 and drive mechanism 125, which are controllable by controller 121, executing a medication delivery algorithm (MDA) 129 stored in memory 123, which may perform some or all of the functions of the AP application described above, such that user device 105 may be unnecessary for drug delivery device 102 to carry out drug delivery and control. Alternatively, controller 121 may act to control reservoir 124 and drive mechanism 125 based on signals received from user app 160 executing on a user device 105 and communicated to drug delivery device 102 via communication link 194. Drive mechanism 125 may operate, for example, to longitudinally translate a plunger through the reservoir, so as to force the liquid drug through an outlet fluid port to needle/cannula 186.

In an alternate embodiment, drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide, GLP-1, glucagon, or another drug. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common needle/cannula 186.

Drug delivery device 102 may be optionally configured with a user interface 127 providing a means for receiving input from the user and a means for outputting information to the user. User interface 127 may include, for example, light-emitting diodes, buttons on a housing of drug delivery device 102, a sound transducer, a haptic technology (e.g., a vibrator), a micro-display, a microphone, an accelerometer or an IMU or similar sensing device for detecting motions of the device or user gestures (e.g., tapping on a housing of the device) or any other type of interface device that is configured to allow a user to enter information and/or allow drug delivery device 102 to output information for presentation to the user (e.g., alarm signals or the like).

Drug delivery device 102 includes a patient interface 186 for interfacing with the user to deliver the liquid drug. Patient interface may be, for example, a needle, cannula, a microneedle array, or a cannula disposed at the end of a tubing set, for delivering the drug into the body of the user (which may be done subcutaneously, intraperitoneally, or intravenously). Drug delivery device 102 further includes a mechanism for inserting the needle/cannula 186 into the body of the user, which may be integral with or attachable to drug delivery device 102. The insertion mechanism may comprise, in one embodiment, an actuator that inserts the needle/cannula 186 under the skin of the user and thereafter retracts the needle, leaving the cannula in place. The actuator may be triggered by user device 105 or may be a manual firing mechanism comprising springs or other energy storing mechanism, which causes the needle/cannula 186 to penetrate the skin of the user. A similar mechanism may be present to insert sensors.

In one embodiment, drug delivery device 102 includes a communication interface 126, which may be a transceiver that operates according to one or more radio-frequency protocols, such as Bluetooth®, Bluetooth® low energy, Bluetooth® smart, Wi-Fi, near-field communication, cellular, or a cellular modem capable of hand-off to a Wi-Fi connection and vice-a-versa, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount. In one embodiment, analyte sensor 108 may be integral with drug delivery device 102.

Drug delivery device 102 further includes a power source 128, such as a battery, a piezoelectric device, an energy harvesting device, or the like, for supplying electrical power to controller 121, memory 123, drive mechanisms 125 and/or other components of drug delivery device 102.

Drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, JOB, insulin remaining, and the like and to cause controller 121 to activate drive mechanism 125 to deliver the medication from reservoir 124. MDA 129 may take as input data received from the analyte sensor 108 or from user app 160.

The reservoirs 124, 124-2 may be configured to store drugs, medications, or therapeutic agents suitable for automated delivery, such as insulin, Pramlintide, GLP-1, co-formulations of insulin and GLP-1, glucagon, morphine, blood pressure medicines, chemotherapy drugs, fertility drugs or the like.

Drug delivery device 102 may be a wearable device and may be attached to the body of a user, such as a patient or diabetic, at an attachment location and may deliver any therapeutic agent, including any drug or medicine, such as insulin or the like, to a user at or around the attachment location. A surface of drug delivery device 102 may include an adhesive on the surface of the drug delivery device or provided as a separate adhesive patch, to facilitate attachment to the skin of a user.

When configured to communicate with an external device, such as the user device 105 or the analyte sensor 108, drug delivery device 102 may receive signals over the wired or wireless link 194 from the user device 105 or from the analyte sensor 108. The controller 121 of drug delivery device 102 may receive and process the signals from the respective external devices as well as implementing delivery of a drug to the user according to a diabetes treatment plan or other drug delivery regimen.

Accessory Device

Optional accessory device 107 may be, a wearable smart device, for example, a smartwatch (e.g., an Apple Watch®), smart eyeglasses, smart jewelry, a global positioning system-enabled wearable, a wearable fitness device, smart clothing, or the like. Similar to user device 105, the accessory device 107 may also be configured to perform various functions including controlling drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality. In some instances, accessory device 107 may also include sensors of various types.

Analyte Sensor

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of drug delivery device 102. The memory 132 may be configured to store information and programming code 136.

The analyte sensor 108 may be configured to detect one or multiple different analytes, such as glucose, lactate, ketones, uric acid, sodium, potassium, alcohol levels or the like, and output results of the detections, such as measurement values or the like. The analyte sensor 108 may, in an exemplary embodiment, be configured as a continuous glucose monitor (CGM) to measure blood glucose values at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller, or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from drug delivery device 102, in various embodiments, the analyte sensor 108 and drug delivery device 102 may be incorporated into the same unit. That is, in various examples, the analyte sensor 108 may be a part of, and integral with, drug delivery device 102 and contained within the same housing as drug delivery device 102 or an attachable housing thereto. In such an example configuration, the controller 121 may be able to implement the functions required for the proper delivery of the medication alone without any external inputs from user device 105, the cloud-based services 111, another sensor (not shown), the optional accessory device 106, or the like.

Cloud-Based Services

Drug delivery system 100 may communicate with or receive services from a cloud server 122 providing cloud-based services 111. Services provided by cloud server 112 may include data storage that stores personal or anonymized data, such as blood glucose measurement values, historical IOB or TDI, prior carbohydrate-compensation dosage, exercise and activity levels, other medication use, weight, height and similar physiological data, and other forms of data. In addition, the cloud-based services 111 may process anonymized data from multiple users to provide generalized information related to TDI, insulin sensitivity, IOB and the like. The communication link 115 that couples the cloud server 112 to other components of system 100, for example, devices 102, 105, 106, 108 of system 100 may be a cellular link, a Wi-Fi link, a Bluetooth® link, or a combination thereof.

Communication Links

The wireless communication links 115 and 191-196 may be any type of wireless link operating using wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 126, 135, 154 and 174. Communication link 115 may be implemented as, for example, a Wi-Fi communication link, a cellular communication link (e.g., 5G, LTE, LTE-M, or the like) or other similar data communication link.

Operational Example

In an operational example, user application 160 implements a graphical user interface that is the primary interface with the user and is used to start and stop drug delivery device 102, program basal and bolus calculator settings for manual mode as well as program settings specific for automated mode (hybrid closed-loop or closed-loop).

User app 160, provides a graphical user interface 158 that allows for the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

User app 160 may be configured to operate in a manual mode in which user app 160 will deliver insulin at programmed basal rates and user-defined bolus amounts with the option to set temporary basal profiles. The controller 121 will also have the ability to function as a sensor-augmented pump in manual mode, using sensor glucose data provided by the analyte sensor 108 to populate the bolus calculator.

User app 160 may be configured to operate in an automated mode in which user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm.

Description of Embodiments

SIM cards, along with cellular radios providing cellular connectivity are ubiquitous in daily life and allow constant online connectivity for a wide variety of devices. This includes the possibility of durable, semi-disposable and disposable wearables of the type used in system 100 acquiring consistent online connectivity without significant action by the users and without the need for a user device 105 to provide cellular data connectivity. Such a capability provides opportunities to utilize a wide range of communication modalities directly on the wearables that may not be otherwise available without significant user workarounds and/or the availability of a separate device that provides cellular data capabilities, such as user device 105.

Similarly, the wide availability of Wi-Fi access in homes, schools, and businesses also enables communication between wearables or between a wearable and a cloud server without such devices leveraging a user device 105 to relay between the wearable and a network resource. Network resources may include, for example, cloud-based services, cloud computing applications and caregivers wishing to oversee and monitor the well-being of users of automated drug delivery systems.

During the course of a day, a person using a communication-enabled wearable may travel within their home, a school, or a business without having their smartphone nearby, and thus, may be out of Bluetooth communication range with other components of system 100. In the event a wearable attempts to emit a wireless message to alert a caregiver of a critical condition (e.g., severe dysglycemia), it would be desirable for the wearable to have the ability to switch communication modalities and appropriate electronic assets from Bluetooth to Wi-Fi or cellular and communicate with a distant caregiver. In various embodiments, with the presence of a cellular radio and a SIM card, the location of the device may be known with the help of triangulation technique. This can be useful to locate a device or a person in case of emergency or family member tracking by caregivers.

Figure 2:
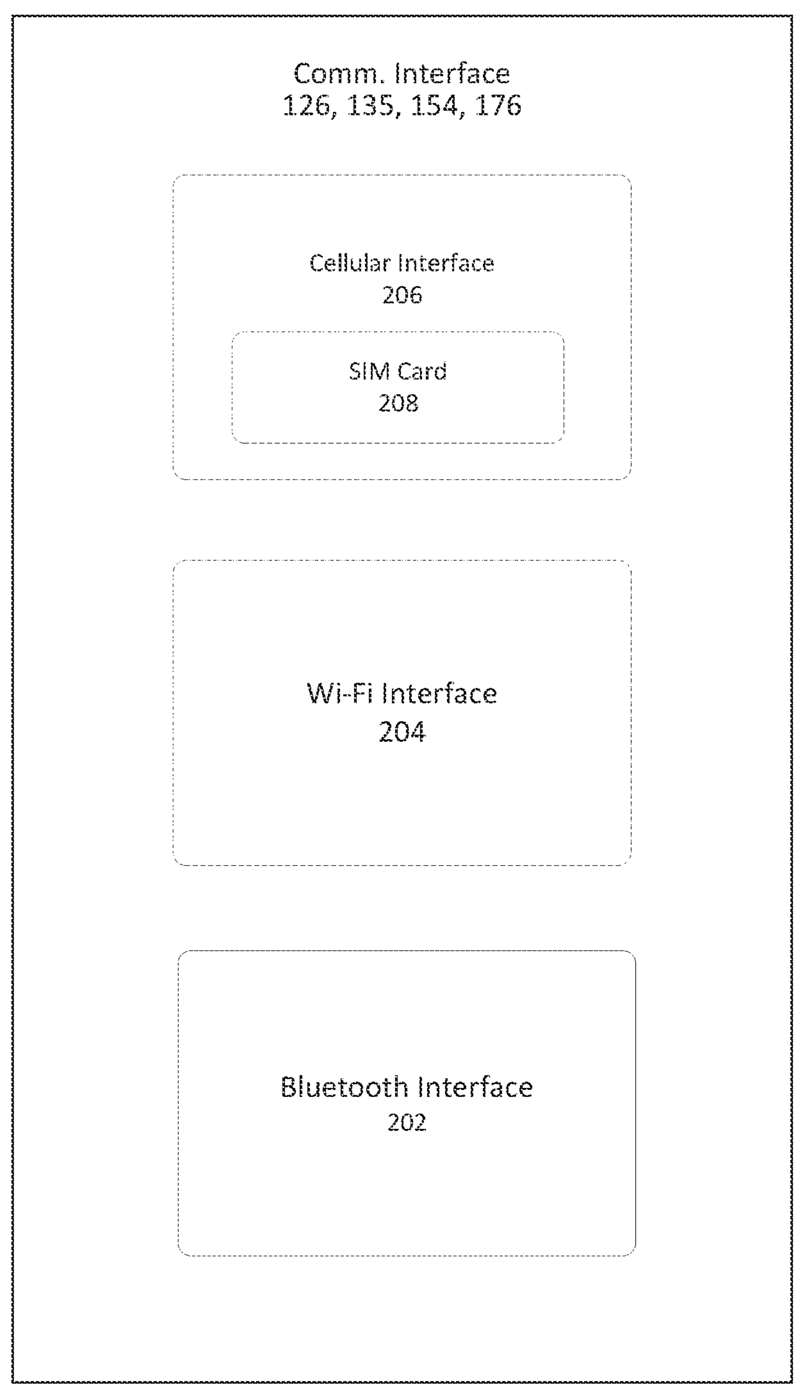
FIG. 2 is a more detailed block diagram of the communication interface used by each component of the automated drug delivery system of FIG. 1.

As previously described, and as shown in FIG. 1, each of the user device 105, drug delivery device 102, accessory device 106 and analyte sensor 108 are configured with a communications interface 154, 126, 174 and 135, respectively. In various embodiments, communication interface 154, 126, 174 and 135 may be configured, as shown in FIG. 2, with a Bluetooth interface 202, an optional Wi-Fi interface 204 and/or an optional cellular interface 206 utilizing an activated SIM card 208.

In some embodiments, especially with wearable components of system 100, for example, drug delivery device 102 and analyte sensor 108, a Wi-Fi interface 204 and/or a cellular interface 206 may be built into the device or may be provided in a connectable module or in a durable portion of the device. For example, drug delivery device 102 may include a semi-durable device which may include a module containing durable components (e.g., controller 121, memory 123, sensors 184, etc.) that may be utilized multiple times and connectable to a disposable portion of the device which may include components (e.g., reservoir 124, needle/cannula 186, and perhaps power source 128) that may be replaced each time the reservoir is drained. In such cases, it is desirable that the Wi-Fi or cellular interface 206, 208 be disposed in the durable portion of the wearable. In other embodiments, drug delivery device 102 may be a disposable device having a programmable SIM card 208 which may be programmed via communications interface 126 from a previous drug delivery device 102 and moved to a new drug delivery device 102. Note that it is presumed that user device 105 will always be provided with all three modes of communication.

Components of system 100 may automatically switch from one communication modality to another, for example, when a wearable component of system 100 is constrained by battery energy. Wi-Fi access credentials can be pre-programmed or shared via a Bluetooth exchange with user device 105. In the case when a Wi-Fi access point is open, and the message is a high priority alert, the wearable could send the message. Such a message could be encrypted. Programming of the wearable while in a Wi-Fi interaction would preferably be disallowed. When both the Bluetooth connection to the user's smartphone and Wi-Fi access is present, the wearable could automatically prefer the Bluetooth protocol so as to not increase the battery energy requirement by switching to Wi-Fi. In an additional embodiment, the wearable may communicate via Wi-Fi to reach user device 105 that is out of Bluetooth communication range. In this mode, the Wi-Fi network would serve as a relay. The wearable would thus be provisioned to dynamically change communication protocols to achieve communication with a caregiver or cloud computing resource. In certain circumstances where urgent communication may be required, communication may be attempted across all available interfaces, such as Wi-Fi, Bluetooth, and cellular interfaces, to ensure that a successful communication is executed.

Because continuous communication using the Wi-Fi or cellular interfaces 206, 208, is likely to consume too much battery energy in a wearable component of system 100, it is possible that the components may only use these communication modalities for high-priority messaging, to conserve battery energy. When high-priority messaging is no longer required, the communications interfaces 206, 208 can be turned off to prolong battery life. Additionally, when a lower power communication mode is available, the communication arbiter in drug delivery device switches to this mode. Such a transition happens automatically and seamlessly.

Inter-Component Communications (330)—In one embodiment, any of the communication modalities may be used for inter-component communications via communication links 115, 191, 193, 194, 195 and 196. The components of system 100 may have a hierarchy of preferred communications. For example, in one embodiment, the preferred modality for inter-component communications may be Bluetooth interface 204. In some instances, inter-component communications via Bluetooth interface 204 may be unreliable or unavailable due to, for example, interference or when the components are out of Bluetooth communications range with respect to each other. In the event the devices are unable to communicate via Bluetooth interface 204, the components may then attempt to communicate via the Wi-Fi interface 206. The Wi-Fi communications may be via an existing Wi-Fi network provided by a local hotspot or may be accomplished in a peer-to-peer mode. Alternatively, one of the components of system 100 may be configured and designated to act as a Wi-Fi hotspot to which the other components of the system may connect and receive an IP address. In some instances, inter-component Wi-Fi communication may also not be possible, for example, when the devices are not near an existing hotspot. In such a case, the components of system 100 may then attempt inter-component communication via a cellular interface 206.

In one embodiment, inter-component communication 330 may be accomplished via a cloud-based service 111 executing on a cloud server 112 to provide inter-component communication service 330. A first component may upload data to the cloud server and the cloud server may then download the data to a second component. For example, analyte sensor 108 may be provided with a Wi-Fi interface 206 or cellular interface 206 and may upload blood glucose readings to a cloud server. User device 105 and/or drug delivery device 102, is also provided with a Wi-Fi interface 206 or cellular interface 206 and may then connect to the cloud server to receive the readings uploaded by analyte sensor 108. In certain embodiments, the cloud server may modify the data received from the first component before downloading it to the second component (e.g., the data may be reformatted, etc.). In some embodiments, the first and second components may connect to the cloud server using different communication modalities and exchange data via the cloud server.

Figure 3:
FIG. 3 is a block diagram showing various cloud-based services that may be accessed by the automated drug delivery system of FIG. 1.

In some embodiments, any component of system 100, may communicate with a cloud server directly, without the need of a user device 105 having Wi-Fi and cellular communications capability. The cloud server 112 may provide a plethora of cloud-based services 111 directly to the components of system 100, as shown in FIG. 3. Such cloud-based services 111 will now be discussed. It should be noted that, while several specific cloud-based services 111 are discussed below and shown in FIG. 3, all such services are optional and may or may not be provided by the manufacturer of system 100. Additionally, some of cloud-based services 111 may be more appropriate for particular components of system 100 and not for others.

Figure 4:
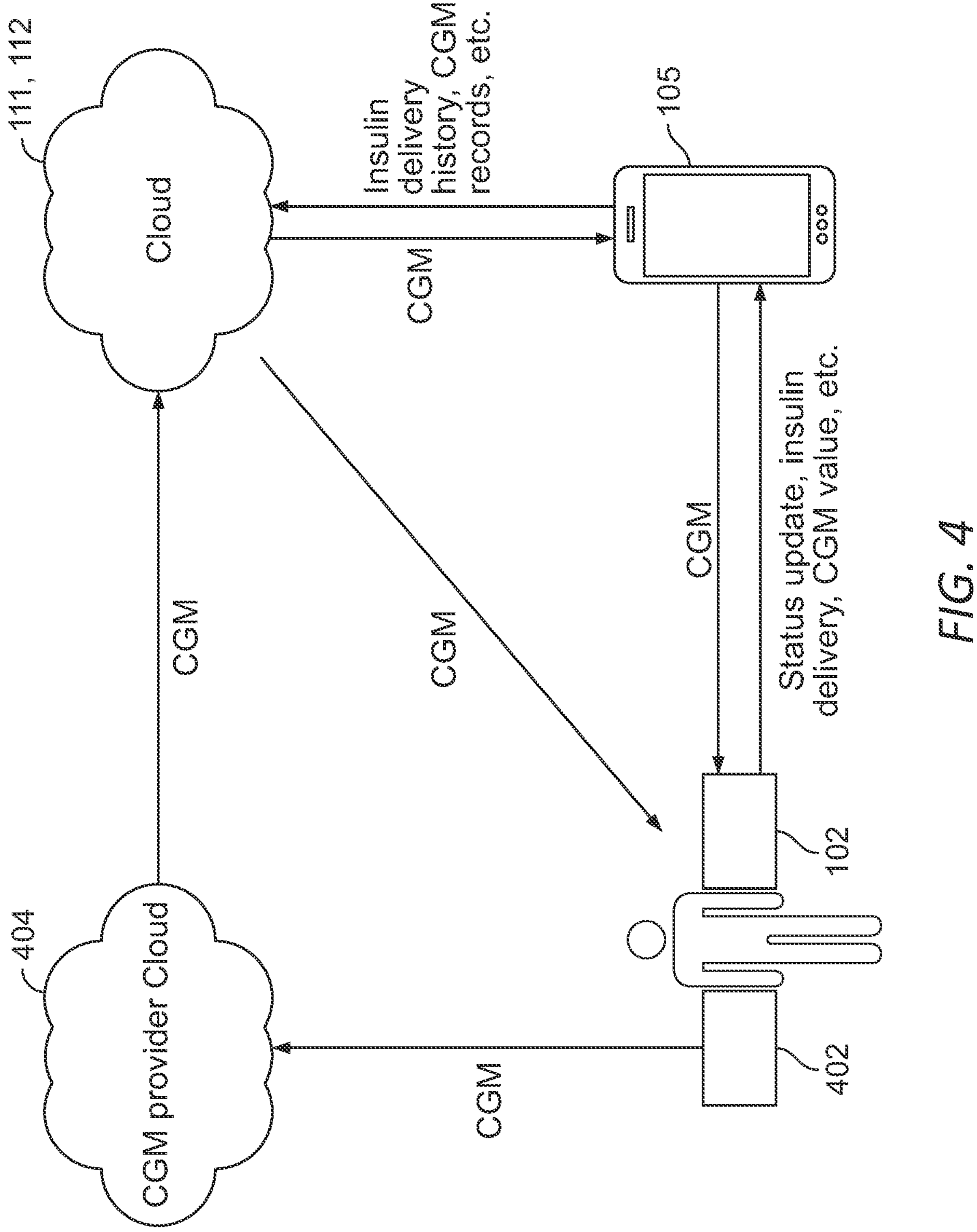
FIG. 4 is a block diagram showing a method for integrating a new glucose monitor with the automated drug delivery system of FIG. 1.

Adopting a new CGM sensor (i.e., a model of CGM sensor that system 100 has not worked with before, perhaps from a different manufacturer) into system 100 is a tedious process requiring reprogramming of various components of system 100 and obtaining approval for use of the new CGM with system 100. Such an effort can be costly, time consuming and may take significant amount of time to support the new CGM sensor. For example, if MDA 129 is executed on drug delivery device 102, then the CGM specific handshake must be implemented on the drug delivery device 102 for the new CGM and drug delivery device 102 to interoperate successfully to read CGM readings, needed by MDA 129. A similar problem exists when MDA 161 is executed on user device 105 as part of user app 160. In one embodiment, system 100 addresses this problem using the inter-component communication service 330 of cloud-based services 111, as shown in FIG. 4. In this embodiment, new CGM 402 uploads CGM readings to a cloud server 404, for example, a cloud server provided by the manufacturer of CGM 402. Preferably, new CGM 402 will be configured with a Wi-Fi interface or a cellular interface that it is to be able to communicate CGM readings to cloud server 404 independent of other components of system 100. Cloud server 404 may interpret, format, or otherwise place the CGM readings in a condition wherein they can be made available, preferably via an API, for download. Cloud server 112, providing cloud-based services 111, may download the CGM readings from cloud server 404. Cloud server 112 may then place the CGM readings in a format where they may be interpreted by user device 105 or drug delivery device 102. CGM readings are then directly downloaded to either or both of user device 105 or drug delivery device 102 via communication link 115, where they may be used as inputs to MDA 161 or MDA 129, respectively. Alternatively, user device 105 may act as a relay between cloud server 112 and drug delivery device 102, wherein the CGM readings may be downloaded from cloud server 112 to user device 105 via communication link 115, after which user device 105 downloads the CGM readings to drug delivery device 102 for use by MDA 129. Communication link 115 may be implemented as, for example, a Wi-Fi interface 204 or a cellular interface 206. Using either of these schemes, a new CGM 402 from a new manufacturer may easily be integrated into system 100.

Remote Execution of MDA—Cloud-based services 111 may include running MDA 129 on a cloud server and controlling drug delivery device 102 remotely. In such a case, MDA 129 on the cloud server may receive readings from analyte sensor 108 via the Wi-Fi interface 206 or cellular interface 206 of communications interface 135 and may use the readings as input to MDA 129, which calculates and controls the size and timing of the delivery of a liquid drug by drug delivery device 102. In this case, drug delivery device 102 would also be in communication with the cloud server via Wi-Fi interface 204 or cellular interface 206 of communications interface 126. In such a case, wherein communications between drug delivery device 102 and cloud-based services 111 and analyte sensor 108 and cloud-based services 111 is crucial for the proper delivery of the liquid drug, and, as such is considered high-priority, the preferred modality of communication may be cellular interface 206, as the components 102 and 108 are more likely to be in proximity to a cellular tower than to a Wi-Fi hotspot to which they are able to connect. Alternatively, the preferred modality of communication may be via Wi-Fi interface 206 and communications via cellular interface 206 may be used only when the devices fail to communicate via Wi-Fi interface 206.

Device Updates (310)—Most components of system 100 may rely on periodic software updates for significant portions of their functionality. The inclusion of a Wi-Fi interface 206 or cellular interface 206 in some or all of the components of system 100 can allow these devices to automatically receive software updates via device update service 310 without significant user interactions, based on an online framework maintained by the manufacturers.

Automated Ordering of Supplies/Maintenance (312)—The presence of a Wi-Fi interface 206 or cellular interface 206 on one or more of the components of system 100 can also facilitate the automated tracking of the liquid drug that is being delivered by drug delivery device 102. Once the user accepts and supplies payment and prescription information, the cloud-based service 212 can automatically determine the quantity of the liquid drug that has been consumed and submit an order on behalf of the user for a new quantity of the liquid drug to ensure the user does not run out. Further, the system can also determine if any consumable components with a shelf life need to be replaced (e.g., internal batteries, sterile reservoirs, etc.) and place those orders Prescription Control (314)—As implied above, the ability to communicate directly with the cloud server can also allow the components of system 100 to be automatically activated only by a particular user with a specific prescription that is specifically linked to their physician. For example, a particular drug delivery device 102 may be linked to a prescription provided by a user's physician. The physician may enable the particular drug delivery device to be activated and made ready for use by communicating directly with the particular drug delivery device 102 or via a cloud server 112, for example. Prescriptions and drug delivery devices can be linked in cloud-based services 111 and only when properly linked, would the corresponding drug delivery device be functional and available for use by a user. Thus, the risk of system 100 being utilized out of prescription and inappropriately used can be mitigated. Cloud-based drug interaction screening may prevent multiple physicians from prescribing medications that may interfere with the therapy currently underway.

Physician Data Sharing (316)—As an extension of the prescription control above, the user's liquid drug use data and other data, for example, blood glucose readings, can also be shared with a physician directly or via cloud server 112 through the use of the Wi-Fi interface 206 or cellular interface 206, in real time as system 100 is utilized, without special additional actions by the user beyond the initial prescription verification. This allows the physician or other HCP to ensure the user's clinical care is maintained properly.

Training Validations (318)—As further extension of the verification and data sharing activities previously discussed, a key requirement for the use of insulin pumps is ensuring that the user can utilize system 100 appropriately through training. The system can both verify that the user has gone through training automatically at the time of the physician validation, and also automatically inform the user if any additional training is needed to execute a specific functionality of system 100.

Caretaker Data Sharing (320)—The data sharing capabilities previously described can also be extended to easily allow users, for example, a caretaker, to define others to receive their system use data without taking any specific actions beyond defining an email address, phone number, or other contact information. To set up the data sharing, in one embodiment, the user may enter identifying information of the caretaker, for example, an email address of the person to receive the data via user app 160 on user device 105. The configuration can then be downloaded to drug delivery device 105 or analyte sensor 108 or uploaded to the cloud-based service. Alternatively, an interface, for example, user interface 127 on drug delivery device 105 or user interface 137 on analyte sensor 108 can allow the user to enter the identifying information of the person(s) to receive the data, and, at the simplest level, an e-mail summary can be provided to connected caretakers at regular intervals. More advanced implementations can allow caretakers to automatically receive real time data on their personal devices via specialized apps, without requiring significant additional time investment by the users of system 100.

Region Based Functionalities (322)—A Wi-Fi interface 206 or cellular interface 206 can also be utilized to automatically provide system functions that vary depending on the current region in which system 100 is located. For example, different regulatory and market environments mean certain functionalities, such as access to specific networked sensors, may not be available or approved. In those cases, rather than creating a new product for each region, inclusion of localization capabilities can allow activation/deactivation of specific product features or functions. Further, drug delivery device 102, analyte sensor 108, and/or accessory device 106 may receive updated time/date information from an external signal through Wi-Fi interface 206 or cellular interface 206. In this manner, the current time on drug delivery device 102, analyte sensor 108, and/or accessory device 106 may remain current and drug deliveries, analyte sensing activity, or other activities may be tagged with accurate time/date information, and autocorrected for the user's current time zone, regardless of whether the device(s) are able to communicate with user device 105 (such as a smartphone).

Data Persistence (324)—Via this cloud-based service, system 100 not only has the capability to provide data to different stakeholders (such as healthcare providers or caretakers) but also has the capability to automatically store data generated by system 100 on a separate entity, such as a cloud server. For instance, the presence of a Wi-Fi interface 206 or cellular interface 206 means that the user can automatically continue using system 100 after a reset of the storage of any component of system 100 by merely providing their credentials within system 100 as if their use was continuous. Further, even if the total amount of available history exceeds the available storage of system 100, additional data can continue to be stored in the cloud.

Long Term User Insights (326)—This cloud-based service may provide complex calculations to gain long-term insights through the use of the data collected in stored in the cloud by data persistence service 324. The data can be utilized to provide users with insights over time. For instance, as adolescents enter adulthood, the insulin needs of these users change dramatically—these years-long insights may not be feasible, and in fact, not optimal due to potential data losses, to be calculated within components of system 100. However, such insights can easily be provided to users through from a cloud service 324 via Wi-Fi interface 206 or cellular interface 206.

AID Algorithm "Big Data" Adaptivity (326)—Cloud-based service 326 allows the seamless integration of more complex interactions requiring significant computational loads that are not feasible to be executed individual components of system 100. The automated availability of significant amounts of diabetes care data means a wide range of "big data" analytics can be utilized to update any computations within components of system 100, for example, medication delivery algorithm 129, in real time. For instance, the user's glucose and insulin delivery trends can be compared against a similar library of many users with similar trends and responses. Thereafter, specific AID algorithm settings that would present the best glucose outcomes for the user can be selected and sent to individual components of system 100, for example, drug delivery device 102.

In an additional embodiment of the system, when at least one component of system 100 is provided with a cellular interface 206 with an activated SIM card 208, (e.g., user device 105) the potential rate of inter-component connectivity can be inferred or predicted from the estimated rate of connectivity of the cellular interface 206 to determine whether adjustments need to be made, for example, in the operation of MDA 129, to compensate for poor connectivity rates. For example, cellular interface 206 can provide the total connection idle time between scanning and system response to various Bluetooth system components. Over time, if these readings increase compared to a baseline, this may indicate that the system is at a location with high Bluetooth interference, potentially leading to a lower inter-component connectivity rates. Given this information, various modifications may be made to MDA 129. For example, timeout before which system 100 stops waiting for new blood glucose values from analyte sensor 108 before determining the proper quantity and timing of additional doses of the liquid drug may be lengthened.

Alternatively, user device 105 can also provide connectivity with typical cellular services. As the connectivity between user device 105 and the cellular service decreases, a correlation can be made that system 100 may also be in a location without interference, leading to similar compensation methods.

Figure 5:
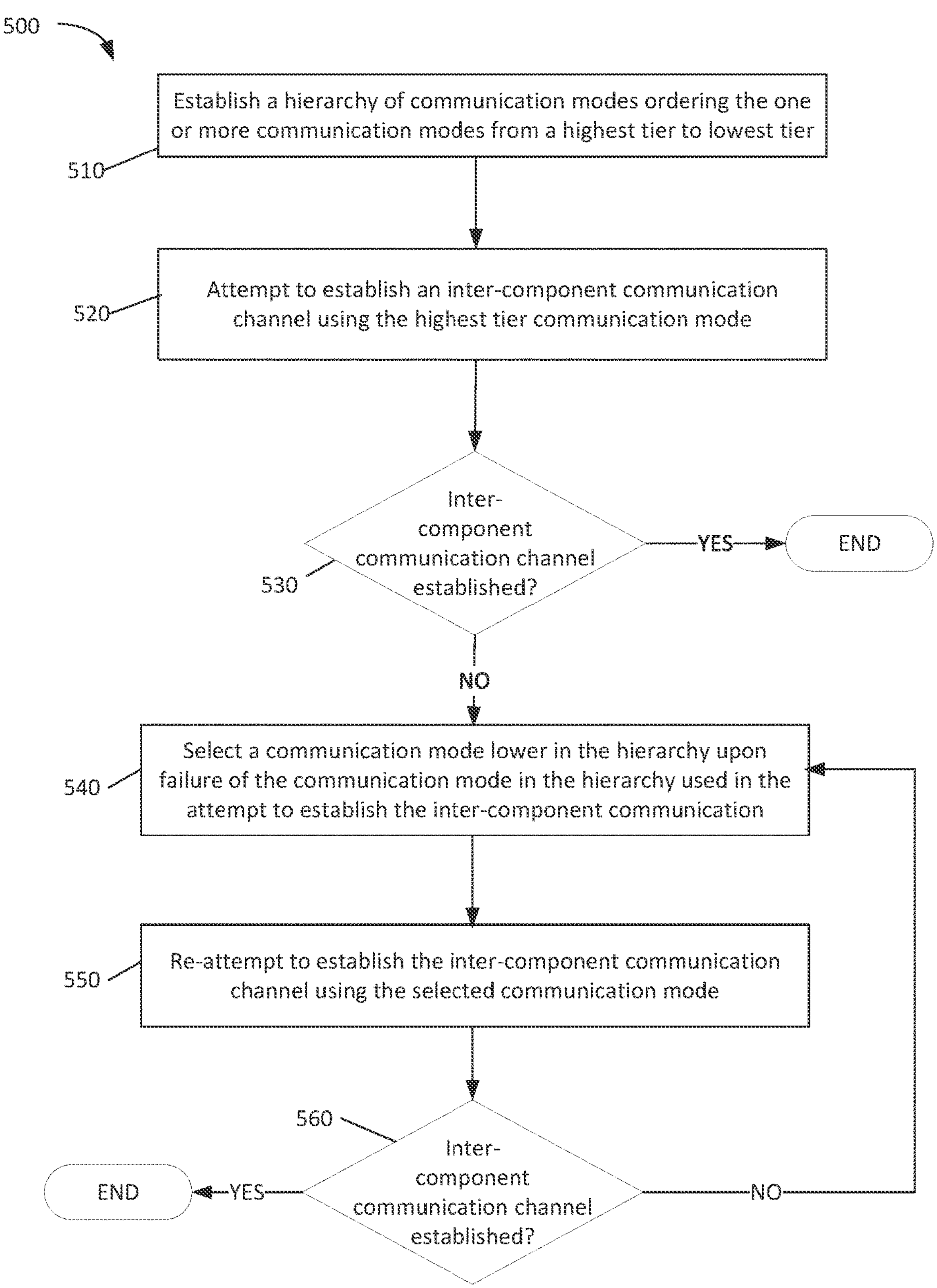
FIG. 5 illustrates a flowchart of an example process for managing communications in wearable drug delivery system.

FIG. 5 illustrates a flowchart of an example process for managing communications in a drug delivery system. A processor may be operable to perform a number of functions such as those described herein. In the process 500, the processor may be operable, at 510, to establish a hierarchy of communication modes ordering the one or more communication modes from a highest tier to lowest tier. For example, the highest tier may be Bluetooth and a lower tier may be Wi-Fi and a lowest tier may be cellular communication. Cellular communication may be assigned the lowest tier because it may incur additional financial costs compared to Bluetooth or Wi-Fi.

At 520, the processor may be operable to attempt to establish an inter-component communication channel using the highest tier communication mode in the hierarchy. For example, a preset number of attempts via the highest tier communication mode may be made.

At 530, in response to the inter-component communication channel being established (i.e., a "YES" response), the process 500 ends. Alternatively, if, at 530, it is determined an inter-component communication channel is not established (i.e., a "NO" response), the process 500 may proceed to 540. At 540, the processor may select a communication mode lower in the hierarchy upon failure of the communication mode in the hierarchy used in the attempt to establish the inter-component communication. For example, if the processor attempted to make a Bluetooth communication between a controller and a sensor, the processor may select, for example, Wi-Fi, as a communication mode lower in the hierarchy. Using the selected communication mode, the processor at 550 may re-attempt to establish the inter-component communication channel using the selected communication mode (e.g., Wi-Fi). The processor, at 560, may confirm that the inter-component communication channel is established. If the inter-component communication channel is established (i.e., a "YES" determination), the process 500 proceeds to END. Alternatively, if the inter-component communication channel is not established (i.e., a "NO" determination), the process 500 returns to step 540.

The following examples pertain to various embodiments of the systems and methods disclosed herein for implementation of an automated drug delivery system having a double reservoir pumping mechanism.

Example 1 is a first embodiment of a method of inter-component communication in an automated drug delivery system comprising a plurality of components, each component having one or more modes of communication wherein the method comprises establishing a hierarchy of communication modes ordering the communication from a highest tier to a lowest tier, attempting to establish an inter-component communication channel using the highest tier communication mode, selecting a communication mode lower in the hierarchy upon failure of a communication mode higher in the hierarchy and re-attempting the intercomponent communication using the selected mode.

Example 2 is an extension of Example 1, or any other example disclosed herein, wherein an ordering of the communication modes in the hierarchy is dependent on an importance of the inter-component communication to safe operation of the automated drug delivery system.

Example 3 is an extension of Example 1, or any other example disclosed herein, wherein Bluetooth is the highest tier communication mode.

Example 4 is an extension of Example 1, or any other example disclosed herein, wherein various components of the automated drug delivery system are configured with one or more communication modes selected from a predetermined set of communication modes and further wherein components may be configured differently.

Example 5 is an extension of Example 4, or any other example disclosed herein, wherein one of the set of communication modes is Wi-Fi and further wherein one or more components of the automated drug delivery system are configured with a Wi-Fi radio.

Example 6 is an extension of Example 5, or any other example disclosed herein, wherein a Wi-Fi communication between two components is a peer-to-peer communication.

Example 7 is an extension of Example 6, or any other example disclosed herein, wherein one component in the automated drug delivery system establishes a Wi-Fi hotspot to which other components in the automated drug delivery system can connect.

Example 8 is an extension of Example 5, or any other example disclosed herein, wherein a Wi-Fi communication between two components is via an existing Wi-Fi hotspot.

Example 9 is an extension of Example 4, or any other example disclosed herein, wherein one of the set of communication modes is a cellular data connection and further wherein one or more components of the automated drug delivery system are configured with a cellular radio and an activated SIM card.

Example 10 is an extension of Example 1, or any other example disclosed herein, wherein two components of the automated drug delivery system communicate with each other through a cloud server intermediary and exchange data via the cloud server.

Example 11 is an extension of Example 10, or any other example disclosed herein, wherein the two components communicate with the cloud server via Wi-Fi or cellular communication modes.

Example 12 is an extension of Example 10, or any other example disclosed herein, wherein each of the two components uses a different communication mode to communicate to the cloud server.

Example 13 is an extension of Example 1, or any other example disclosed herein, wherein components of the automated drug delivery system automatically switch to a different mode of communication when necessary for maintenance of a communication channel.

Example 14 is an extension of Example 13, or any other example disclosed herein, wherein the two components automatically switch to a communication mode requiring less energy when battery power of either one of the two components is low.

Example 15 is an embodiment comprising a method of providing cloud-based services to components of an automated drug delivery system comprising a plurality of components, each component having one or more modes of communication wherein the method comprises establishing a Wi-Fi or cellular communication channel between a cloud server providing the cloud-based services and one or more components of the automated drug delivery system, and providing the cloud-based service via the communication channels.

Example 16 is an extension of Example 15, or any other example disclosed herein, wherein the cloud-based service is execution of a medication delivery algorithm on the cloud server and remotely controlling delivery of a liquid drug via the automated drug delivery system by the cloud server.

Example 17 is an extension of Example 16, or any other example disclosed herein, wherein a communication channel is established between the cloud server and a drug delivery device of the automated drug delivery system and further wherein the cloud server delivers control signals to the drug delivery device specifying the timing and quantity of the liquid drug to be delivered.

Example 18 is an extension of Example 17, or any other example disclosed herein, wherein a communication channel is established between the cloud server and an analyte sensor, a cloud server receiving readings from the analyte sensor via the communication channel and inputting the readings to the medication delivery algorithm.

Example 19 is an extension of Example 15, or any other example disclosed herein, wherein the cloud-based service provides inter-component communication between components of the automated drug delivery system and further wherein the cloud server receives data from a first component of the automated drug delivery system via first communication channel and delivers the data to a second component via a second communication channel.

Example 20 is extension of Example 19, or any other example disclosed herein, wherein the data is modified by the cloud server before delivery to the second component.

Example 21 is an extension of Example 20, or any other example disclosed herein, wherein the first component is an analyte sensor and wherein the data comprises readings from the analyte sensor and further wherein the second component is a drug delivery device or user device executing a medication delivery algorithm.

Example 22 is an extension of Example 15, or any other example disclosed herein, wherein the cloud-based service provides automated software updates to one or more components of the automated drug delivery system.

Example 23 is an extension of Example 15, or any other example disclosed herein, wherein the cloud-based service determines that a user's supplies related to the automated drug delivery system have reached a predetermined level or have an upcoming shelf-life expiration and further wherein the cloud-based service automatically re-orders supplies on the user's behalf.

Example 24 is an extension of example 23, or any other example disclosed herein, wherein the user has previously supplied payment and prescription information to the cloud-based service.

Example 25 is an extension of example 15, or any other example disclosed herein, wherein the cloud-based service provides automated activation of components of the automated drug delivery system after verifying a prescription for use of the automated drug delivery system.

Example 26 is an extension of Example 15, or any other example disclosed herein, wherein the cloud-based service receives data from one or more components of the automated drug delivery system and makes the data available to a physician of a user of the automated drug delivery system.

Example 27 is an extension of Example 15, or any other example disclosed herein, wherein the cloud-based service provides training verification that verifies that a user of the automated drug delivery system has completed required training before the automated drug delivery system is activated.

Example 28 is an extension of Example 15, or any other example disclosed herein, wherein the cloud-based service receives data from one or more components of the automated drug delivery system and makes the data available to a caretaker of a user of the automated drug delivery system.

Example 29 is an extension of Example 28, or any other example disclosed herein, wherein the user provides identifying information of the caretaker via a user interface of one of the components of the automated drug delivery system and further wherein the one component sends the identifying information to the cloud-based service.

Example 30 is an extension of Example 15, or any other example disclosed herein, wherein the cloud-based service provides region-based functionalities to the automated drug delivery system.

Example 31 is an extension of Example 30, or any other example disclosed herein, wherein the region-based functionalities include enabling or disabling various features of the automated drug delivery system due to region-specific approvals.

Example 32 is an extension of Example 15, or any other example disclosed herein, wherein the cloud-based service receives data from one or more components of the automated drug delivery system and stores the data.

Example 33 is an extension of Example 32, or any other example disclosed herein, wherein all or a portion of the stored data may be downloaded for use by any component of the automated drug delivery system.

Example 34 is an extension of Example 32, or any other example disclosed herein, wherein the cloud-based service provides long-term trend analysis of the data and further wherein results of the analysis may be provided to a user, physician, or caretaker.

Example 35 is an extension of Example 15, or any other example disclosed herein, wherein the data uploaded to the cloud-based services combined with data from other users for analysis.

Example 36 is an extension of Example 35, or any other example disclosed herein, wherein the cloud-based service compares uploaded data to data uploaded from a plurality of other users to predict trends for a user of the automated drug delivery system.

Example 37 is an extension of Example 36, or any other example disclosed herein, wherein a medication delivery algorithm of the automated drug delivery system modifies delivery of a liquid drug based on the predicted trends.

Example 38 is a third embodiment comprising a method executed by one or more components of an automated drug delivery system, wherein each component is configured with one or more communication modes, at least one component of the system having a cellular data communication mode, the method comprising analyzing performance of the cellular mode of communication to predict potential communication difficulties in other communication modes and modifying operation of the automated drug delivery system to compensate for the potential communication difficulties.

Example 39 is an extension of Example 38, or any other example disclosed herein, wherein the modifying comprises selecting a different communication mode for inter-component or component-to-cloud communications.

Example 40 is an extension of Example 38, or any other example disclosed herein, wherein the modifying comprises modifying behavior or operation of a medication delivery algorithm of the automated drug delivery system.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

To those skilled in the art to which the disclosed subject relates, many modifications and adaptations of the disclosed subject matter may be realized. Implementations provided herein, including sizes, shapes, ratings compositions and specifications of various components or arrangements of components, and descriptions of specific manufacturing processes, should be considered exemplary only and are not meant to limit the claimed subject matter in any way. As one of skill in the art would realize, many variations on implementations discussed herein which fall within the scope of the claimed subject matter are possible. Moreover, it is to be understood that the features of the various embodiments described herein were not mutually exclusive and can exist in various combinations and permutations, even if such combinations or permutations were not made express herein, without departing from the spirit and scope of the disclosed subject matter. Accordingly, the method and apparatus disclosed herein are not to be taken as limitations on the invention but as an illustration thereof.

The invention claimed is:

1. A drug delivery system, comprising:
a processor coupled to a communication interface; and
a plurality of components, each component having one or more modes of communication via a respective communication interface, the processor operable to:
establish a hierarchy of communication modes ordering the one or more communication modes from a highest tier to lowest tier;
attempt to establish an inter-component communication channel using the highest tier communication mode;
select a communication mode lower in the hierarchy upon failure of the communication mode in the hierarchy used in the attempt to establish the inter-component communication; and
re-attempt to establish the inter-component communication channel using the selected communication mode;
a cloud server, wherein the cloud server is configured to operate as a cloud server intermediary and operable to enable two components of the plurality of components to communicate with each other and exchange data via the cloud server.

2. The system of claim 1, wherein:
the one or more modes of communication includes Bluetooth, wherein Bluetooth is the highest tier communication mode of the one or more communication modes.

3. The system of claim 1, wherein various components of the plurality of components are configured differently from one another.

4. The system of claim 1, wherein:
one communication mode of the one or more modes of communication is Wi-Fi, and
one or more components of the plurality of component are configured with a Wi-Fi radio.

5. The system of claim 4, wherein a Wi-Fi communication between two components of the plurality of components is a peer-to-peer communication.

6. The system of claim 5, wherein one component of the plurality of components, comprises:
a processor, and
the processor of the one component of the plurality of components is operable to:
establish a Wi-Fi hotspot available to other components of the plurality of components.

7. The system of claim 1, wherein:
one communication mode of the one or more modes of communication is a cellular data connection; and
one or more components of the plurality of components are configured with a cellular radio and an activated SIM card.

8. The system of claim 1, wherein the two components of the plurality of components are operable to communicate with the cloud server via a Wi-Fi communication mode or a cellular communication mode.

9. The system of claim 8, wherein each of the two components of the plurality of components is operable to use a different communication mode to communicate to the cloud server.

10. The system of claim 8, wherein the two components automatically switch to a communication mode of the one or more modes of communication requiring less energy when battery power of either one of the two components is low.

11. The system of claim 1, wherein each component of the plurality of components is configured to:
automatically switch to a different mode of communication of the one or more modes of communication when necessary for maintenance of a communication channel.

* * * * *